(12) United States Patent
Rapoport et al.

(10) Patent No.: US 6,747,139 B1
(45) Date of Patent: Jun. 8, 2004

(54) NUCLEIC ACID ENCODING HUMAN THYROTROPIN RECEPTOR

(75) Inventors: Basil Rapoport, Santa Monica, CA (US); Sandra McLachlan, Santa Monica, CA (US)

(73) Assignee: Quest Diagnostics Investments, Inc., Wilmington, DE (US)

( * ) Notice: Subject to any disclaimer, the term of this patent is extended or adjusted under 35 U.S.C. 154(b) by 0 days.

(21) Appl. No.: 09/186,350

(22) Filed: Nov. 5, 1998

Related U.S. Application Data

(60) Provisional application No. 60/064,287, filed on Nov. 5, 1997.

(51) Int. Cl.[7] ................................................ C07H 21/04
(52) U.S. Cl. ...................................... 536/23.5; 536/23.1
(58) Field of Search .............................. 536/23.4, 23.1, 536/23.5; 435/69.1, 320.1, 325

(56) References Cited

PUBLICATIONS

Nagayama et al. (1992) Endocrinology 131: 548–552.*

* cited by examiner

*Primary Examiner*—Michael Pak
(74) *Attorney, Agent, or Firm*—Stout, Uxa, Buyan & Mullins, LLP; Donald E. Stout; Greg S. Hollrigel

(57) ABSTRACT

Nucleic acids encoding human thyrotropin receptor and related methods are disclosed. The nucleic acids may have nucleotides deleted and/or replaced to modify the amino acid sequence of human thyrotropin receptor.

3 Claims, 18 Drawing Sheets

A CLEAVAGE SITE 1

```
     317  321  324 327 330   334  337 339 342 345   349   353    358   363
      |    |    |   |   |     |    |   |   |   |     |     |      |    |  ----LH/CG RECEPTOR
     ALNSIPLHIQEYEENILGDSIIVGIYKEKSIKFQDTHNINAHYIYVFFEIEQEDEIIIGF TSH RECEPTOR
     GAAA|AAA|
              IAAA|AAA|
                       IAAA|AAAA|
                                 IAAA|AAA|
                                          IAAA|A|
                                                 A|
                                                   IAAA|AAA|
                                                            IAAA|AAAA|
                                                                      IAAAA|AAAA|
                                                                                IAAAA|AAAAQI
                                                                                           IQAQNQI
```

FIG. 9A

1: [CCGGCTCCCGGGTCTCCTTTGGCCTGGGGTAACCCGGAGTGCAGAGCTGAGAATGAGGCGATTTCGGAGGATGGAGAAATAGCCCGAGTC

91: CCGTGGAAAATGAGGCCGGGACTTGCTGCAGCTGGTGCTGCTGCTCGACCTGCCCAGGACTTGGGCGGAATGGGGTGTTCGTCTCCA
1:                   [M R P A D L L Q L V L L L D L P R D L G G M G C S S P

181: CCCTGCGAGTGCCATCAGGAGGAGGACTTCAGAGTCACCTGCAAGAGTATTCAACGCATCCCCAGCTTACCGCCCAGTACGCAGACTCTG
28:    P C E C H Q E E D F R V T C K D I Q R I P S L P P S T Q T L

271: AAGCTTATTGAGACTCACCTGAGAACTATTCCAAGTCATGCATTTTCTAATCTGCCCAATATTTCCAGAATCTACGTATCTATAGATGTG
58:    K L I E T H L R T I P S H A F S N L P N I S R I Y V S I D V

361: ACTCTGCAGCAGCTGGAATCACACTCCTTCTACAATTTGAGTAAAGTGACTCACATAGAAATTCGGAATACCAGGAACTTAACTTACATA
88:    T L Q Q L E S H S F Y N L S K V T H I E I R N T R N L T Y I

451: GACCCTGATGCCCTCAAAGAGCTCCCCCTCCTAAAGTTCCTTGGCATTTTCAACACTGGACTTAAAATGTTCCCTGACCTGACCAAAGT
118:   D P D A L K E L P L L K F L G I F N T G L K M F P D L T K V

541: TATTCCACTGATATATTCTTTATCTTGAAATTACAGACAACCATGGCTTACTTCAGTCCAAGGATATGCTTTCAATGGGACAAAGCTGGA
148:   Y S T D I F F I L E I T D N P Y M T S I P V N A F Q G L C N

631: GAAACCTTGACACTTGAAGCTGTACAACATGGCTTACTTCAGTCCAAGGATATGCTTTCAATGGGACAAAGCTGGATGCTGTTACCTA
178:   E L T L K L Y N N G F T S V Q G Y A F N G T K L D A V Y L

721: AACAAGAATAAATACCTGACAGTTATTGACAAAGATGCATTTGGAGGAGTATACAGTGGACAAGCTTGCTGGACGTGTCTCAAACCAGT
208:   N K N K Y L T V I D K D A F G G V Y S G P S L L D V S Q T S

811: GTCACTGCCCTTCCATCCAAAGGCCTGGAGCACCTGAAGGAACTGATAGCAAGAAACACTTGGACTCTTAAGAAACTTCCACTTCCTTG
238:   V T A L P S K G L E H L K E L I A R N T W T L K K L P L S L

FIG. 13A

```
901:  AGTTCCTTCACCTCACACGGGCTGACCTTTCTTACCAAGCCACTGCTGTGCTTTAAGAATCAGAGAAAAATCAGAGGAATCCTTGAG
268:   S  F  L  H  L  T  R  A  D  L  S  Y  P  S  H  C  C  A  F  K  N  Q  K  K  I  R  G  I  L  E

991:  TCCTTGATGTGTAATGAGAGCAGTATGCAGAGCTTGCGCAGAGAAAATCTGTGAATGCCTTGAATAGCCCCTCCACCAGGAATATGAA
298:   S  L  M  C  N  E  S  S  M  Q  S  L  R  Q  R  K  S  V  N  A  L  N  S  P  L  H  Q  E  Y  E

1081: GAGAATCTGGGTGACACAGCATTGTGGGTACAAGGAAAAGTCCAAGTTCCAGGATACTCATAACAACGCTCATTATTACGTCTTCTTTGAA
328:   E  N  L  G  D  S  I  V  G  Y  K  E  K  S  K  F  Q  D  T  H  N  N  A  H  Y  Y  V  F  F  E

1171: GAACAAGAGGATGAGATCATTGGTTTTGGCCAGGAGCTCAAAAACCCCCAGGAAGAGACTCTACAAGCTTTTGACAGCCATTATGACTAC
358:   E  Q  E  D  E  I  I  G  F  G  Q  E  L  K  N  P  Q  E  E  T  L  Q  A  F  D  S  H  Y  D  Y

1261: ACCATATGTGGGACAGTGAAGACATGGTGTGTACCCCCAAGTCCGATGAGTTCAACCGTGTGAAGACATAATGGGCTACAAGTTCCTG
388:   T  I  C  G  D  S  E  D  M  V  C  T  P  K  S  D  E  F  N  P  C  E  D  I  M  G  Y  K  F  L

1351: AGAATTGTGGTGTGGTTCGTTAGTCTCCTGGCCCTTTTGGCGGATTTCTGCAATGTCTTTGTCCTGCTTATTCTCCTCACCAGCCACTACAAACTGAAC
418:   R  I  V  V  W  F  V  S  L  L  A  L  L  G  N  V  F  V  L  L  I  L  L  T  S  H  Y  K  L  N

1441: GTCCCCGCTTTCATGTGCAACTTGGCCTTTGCGGATTTCTGCATGGGGATGTACCTGCTGCTCCTCATCGCCTCTGTAGACCTCTACACT
448:   V  P  R  F  L  M  C  N  L  A  F  A  D  F  C  M  G  M  Y  L  L  L  I  A  S  V  D  L  Y  T

1531: CACTCTGAGTACTACAACCATGCCATCGACTGGCAGACAGGCCCTGGGTGCAACACGGCTGGTTTCTTCACTGTCTTTGCAAGCGAGTTA
478:   H  S  E  Y  Y  N  H  A  I  D  W  Q  T  G  P  G  C  N  T  A  G  F  F  T  V  F  A  S  E  L

1621: TCGGTGTATACGCTGACGGTCATCACCCTGGAGCGCTGGTATGCCATGCGCCTTGACCGGAAGATCCGCCTCCGCCTCAGGCAC
508:   S  V  Y  T  L  T  V  I  T  L  E  R  W  Y  A  I  T  F  A  M  R  L  D  R  K  I  R  L  R  H

1711: GCATGTGCCATCATGGTTGGGGGCTGGGTTTGCTGCTTCCTTCTCGCCCTGCTTCTTTTGGGAATAAGTAGCTATGCCAAAGTCAGT
538:   A  C  A  I  M  V  G  G  W  V  C  C  F  L  L  A  L  L  P  L  V  G  I  S  S  Y  A  K  V  S
```

FIG.13B

```
1801: ATCTGCCTGCCCATGGACACCGAGACCCCTCTTGCTCTGGCATATATTGTTTTTGTTCTGAGCGCTCAACATAGTTGCCTTGTCATCGTC
 568:  I  C  L  P  M  D  T  E  T  P  L  A  L  A  Y  I  V  F  V  L  T  L  N  I  V  A  F  V  I  V

1891: TGCTGCTGTCATGTGAAGATCTACATCACAGTCCGAAATCCGCAGTACAACCCAGGGACAAAGATACCAAATTGCCAAGAGGATGGCT
 598:  C  C  C  H  V  K  I  Y  I  T  V  R  N  P  Q  Y  N  P  G  D  K  D  T  K  I  A  K  R  M  A

1981: GTGTTGATCTTCACGGACTTCATATGCATGGCCCCAATCTCATTCTATGCTCTGTCAGCAATTCTGAACAAGCCTCTCATCACTGTTAGC
 628:  V  L  I  F  T  D  F  I  C  M  A  P  I  S  F  Y  A  L  S  A  I  L  N  K  P  L  I  T  V  S

2071: AACTCCAAAATCTTGCTGGTACTCTTCTATCCACTTAACTCCTGTGCCAATCCATTCCTCTATGCTATTTCACCAAGGCCTTCCAGAGG
 658:  N  S  K  I  L  L  V  L  F  Y  P  L  N  S  C  A  N  P  F  L  Y  A  I  F  T  K  A  F  Q  R

2161: GATGTGTTCATCCTACTCAGCAAGTTTGGCATCTGTAAACGCCAGGCTCAGGCACATACCGGGGCAGAGGGTTCCTCCAAAGAACAGCACT
 688:  D  V  F  I  L  L  S  K  F  G  I  C  K  R  Q  A  Q  A  Y  R  G  Q  R  V  P  P  K  N  S  T

2251: GATATTCAGGTTCAAAAGGTTACCCACGACATGAGGCAGGGTCTCCACAACATGGAAGATGTCTATGAACTGATTGAAAACTCCCATCTA
 718:  D  I  Q  V  Q  K  V  T  H  D  M  R  Q  G  L  H  N  M  E  D  V  Y  E  L  I  E  N  S  H  L

2341: ACCCCAAAGAAGAACCAAGGCCAAATCTCAGAAGAGTATATGCAAAACGGTTTTGTAAGTTAACACTACACTACTCACAATGGTAGGGAACTT
 748:  T  P  K  K  Q  G  Q  I  S  E  E  Y  M  Q  T  V  L ]

2431: ACAAAATAATAGTTTCTTGAATATGCATTCCAATCCCAT]
```

FIG.13C

SEQUENCE LISTING

<160> NUMBER OF SEQ ID NOS: 54

<210> SEQ ID NO 1
<211> LENGTH: 138
<212> TYPE: PRT
<213> ORGANISM: human tshr
<220> FEATURE:

<400> SEQUENCE: 1

```
Ser His Cys Cys Ala Phe Lys Asn Gln Lys Lys Ile Arg Gly Ile Leu
  1               5                  10                  15

Glu Ser Leu Met Cys Asn Glu Ser Ser Met Gln Ser Leu Arg Gln Arg
             20                  25                  30

Lys Ser Val Asn Ala Leu Asn Ser Pro Leu His Gln Glu Tyr Glu Glu
         35                  40                  45

Asn Leu Gly Asp Ser Ile Val Gly Tyr Lys Glu Lys Ser Lys Phe Gln
     50                  55                  60

Asp Thr His Asn Asn Ala His Tyr Tyr Val Phe Phe Glu Glu Gln Glu
 65                  70                  75                  80

Asp Glu Ile Ile Gly Phe Gly Gln Glu Leu Lys Asn Pro Gln Glu Glu
                 85                  90                  95
```

```
Thr Leu Gln Ala Phe Asp Ser His Tyr Asp Tyr Thr Ile Cys Gly Asp
            100                 105                 110

Ser Glu Asp Met Val Cys Thr Pro Lys Ser Glu Phe Asn Pro Cys
        115                 120                 125

Glu Asp Ile Met Gly Tyr Lys Phe Leu Arg
130                 135
```

<210> SEQ ID NO 2
<211> LENGTH: 121
<212> TYPE: PRT
<213> ORGANISM: human tshr

<400> SEQUENCE: 2

```
Ser Leu Met Cys Asn Glu Ser Ser Met Gln Ser Leu Arg Gln Arg Lys
 1               5                  10                  15

Ser Val Asn Ala Leu Asn Ser Pro Leu His Gln Glu Tyr Glu Glu Asn
            20                  25                  30

Leu Gly Asp Ser Ile Val Gly Tyr Lys Glu Lys Ser Lys Phe Gln Asp
        35                  40                  45

Thr His Asn Asn Ala His Tyr Tyr Val Phe Phe Glu Glu Gln Glu Asp
    50                  55                  60

Glu Ile Ile Gly Phe Gly Gln Glu Leu Lys Asn Pro Gln Glu Glu Thr
65                  70                  75                  80

Leu Gln Ala Phe Asp Ser His Tyr Asp Tyr Thr Ile Cys Gly Asp Ser
                85                  90                  95

Glu Asp Met Val Cys Thr Pro Lys Ser Asp Glu Phe Asn Pro Cys Glu
            100                 105                 110

Asp Ile Met Gly Tyr Lys Phe Leu Arg
        115                 120
```

<210> SEQ ID NO 3
<211> LENGTH: 70
<212> TYPE: PRT
<213> ORGANISM: Unknown Organism
<220> FEATURE:
<223> OTHER INFORMATION: Description of Unknown Organism:This sequence
      may have come from human LH/CG receptor.

<400> SEQUENCE: 3

```
Phe Ser Ile Phe Glu Asn Phe Ser Lys Gln Cys Glu Ser Thr Val Arg
 1               5                  10                  15

Lys Ala Asp Asn Glu Thr Leu Tyr Ser Ala Ile Phe Glu Glu Asn Glu
            20                  25                  30

Leu Ser Gly Trp Asp Tyr Asp Tyr Gly Phe Cys Ser Pro Lys Thr Leu
        35                  40                  45

Gln Cys Ala Pro Glu Pro Asp Ala Phe Asn Pro Cys Glu Asp Ile Met
    50                  55                  60

Gly Tyr Ala Phe Leu Pro
65                  70
```

<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence:This is a
      mutated TSHR.  TSHR-RK312-313QQ-NET.

<400> SEQUENCE: 4

Ser Leu Met Cys Asn Glu Ser Ser Met Gln Ser Leu Arg Gln Gln Gln
1               5                   10                  15

Ser Val Asn Ala Leu Asn Ser Pro Leu His Gln Glu Tyr Glu Glu Asn
            20                  25                  30

Leu Gly Asp Ser Ile Val Gly Tyr Lys Glu Lys Ser Lys Phe Gln Asp
        35                  40                  45

Thr His Asn Asn Ala His Tyr Tyr Val Phe Phe Glu Glu Gln Glu Asp
    50                  55                  60

Glu Ile Ile Gly Phe Asn Glu Thr Leu Lys Asn Pro Gln Glu Glu Thr
65                  70                  75                  80

Leu Gln Ala Phe Asp Ser His Tyr Asp Tyr Thr Ile Cys Gly Asp Ser
                85                  90                  95

Glu Asp Met Val Cys Thr Pro Lys Ser Asp Glu Phe Asn Pro Cys Glu
            100                 105                 110

Asp Ile Met Gly Tyr Lys Phe Leu Arg
        115                 120

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence:This is a
      mutated TSHR.  TSH-LHR-D5-RK313QQ-NET.

<400> SEQUENCE: 5

Ser Leu Met Cys Asn Glu Ser Ser Met Gln Ser Glu Ser Thr Val Gln
1               5                   10                  15

Gln Ala Asp Ala Leu Asn Ser Pro Leu His Gln Glu Tyr Glu Glu Asn
            20                  25                  30

Leu Gly Asp Ser Ile Val Gly Tyr Lys Glu Lys Ser Lys Phe Gln Asp
        35                  40                  45

Thr His Asn Asn Ala His Tyr Tyr Val Phe Phe Glu Glu Gln Glu Asp
    50                  55                  60

Glu Ile Ile Gly Phe Asn Glu Thr Leu Lys Asn Pro Gln Glu Glu Thr
65                  70                  75                  80

Leu Gln Ala Phe Asp Ser His Tyr Asp Tyr Thr Ile Cys Gly Asp Ser
                85                  90                  95

Glu Asp Met Val Cys Thr Pro Lys Ser Asp Glu Phe Asn Pro Cys Glu
            100                 105                 110

Asp Ile Met Gly Tyr Lys Phe Leu Arg
        115                 120

<210> SEQ ID NO 6
<211> LENGTH: 121
<212> TYPE: PRT
<213> ORGANISM: Artificial Sequence
<220> FEATURE:
<223> OTHER INFORMATION: Description of Artificial Sequence:This is a
      mutated TSHR.  TSH-LHR-D4-NET.

<400> SEQUENCE: 6

Phe Ser Ile Phe Glu Asn Phe Ser Lys Gln Cys Leu Arg Gln Arg Lys
1               5                   10                  15

Ser Val Asn Ala Leu Asn Ser Pro Leu His Gln Glu Tyr Glu Glu Asn
            20                  25                  30

Leu Gly Asp Ser Ile Val Gly Tyr Lys Glu Lys Ser Lys Phe Gln Asp
        35                  40                  45

```
Thr His Asn Asn Ala His Tyr Tyr Val Phe Glu Glu Gln Glu Asp
        50                  55                  60

Glu Ile Ile Gly Phe Asn Glu Thr Leu Lys Asn Pro Gln Glu Thr
 65                  70                  75                  80

Leu Gln Ala Phe Asp Ser His Tyr Asp Tyr Thr Ile Cys Gly Asp Ser
                85                  90                  95

Glu Asp Met Val Cys Thr Pro Lys Ser Asp Glu Phe Asn Pro Cys Glu
                100                 105                 110

Asp Ile Met Gly Tyr Lys Phe Leu Arg
            115                 120

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence:This is a
      mutated TSHR.  TSH-LHR-D5-NET.

<400> SEQUENCE: 7

Ser Leu Met Cys Asn Glu Ser Ser Met Gln Ser Glu Ser Thr Val Arg
 1               5                  10                  15

Lys Ala Asp Ala Leu Asn Ser Pro Leu His Gln Glu Tyr Glu Glu Asn
                20                  25                  30

Leu Gly Asp Ser Ile Val Gly Tyr Lys Glu Lys Ser Lys Phe Gln Asp
            35                  40                  45

Thr His Asn Asn Ala His Tyr Tyr Val Phe Glu Glu Gln Glu Asp
        50                  55                  60

Glu Ile Ile Gly Phe Asn Glu Thr Leu Lys Asn Pro Gln Glu Thr
 65                  70                  75                  80

Leu Gln Ala Phe Asp Ser His Tyr Asp Tyr Thr Ile Cys Gly Asp Ser
                85                  90                  95

Glu Asp Met Val Cys Thr Pro Lys Ser Asp Glu Phe Asn Pro Cys Glu
                100                 105                 110

Asp Ile Met Gly Tyr Lys Phe Leu Arg
            115                 120

<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence:This is a
      mutated TSHR.  TSHR-AAAA305-308-NET.

<400> SEQUENCE: 8

Ser Leu Met Cys Asn Glu Ser Ala Ala Ala Ala Leu Arg Gln Arg Lys
 1               5                  10                  15

Ser Val Asn Ala Leu Asn Ser Pro Leu His Gln Glu Tyr Glu Glu Asn
                20                  25                  30

Leu Gly Asp Ser Ile Val Gly Tyr Lys Glu Lys Ser Lys Phe Gln Asp
            35                  40                  45

Thr His Asn Asn Ala His Tyr Tyr Val Phe Glu Glu Gln Glu Asp
        50                  55                  60

Glu Ile Ile Gly Phe Asn Glu Thr Leu Lys Asn Pro Gln Glu Thr
 65                  70                  75                  80

Leu Gln Ala Phe Asp Ser His Tyr Asp Tyr Thr Ile Cys Gly Asp Ser
                85                  90                  95
```

Glu Asp Met Val Cys Thr Pro Lys Ser Asp Glu Phe Asn Pro Cys Glu
            100                 105                 110

Asp Ile Met Gly Tyr Lys Phe Leu Arg
        115                 120

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence:This is a
      mutated TSHR.  TSHR-AAAA309-312-NET.

<400> SEQUENCE: 9

Ser Leu Met Cys Asn Glu Ser Ser Met Gln Ser Ala Ala Ala Ala Lys
 1               5                  10                  15

Ser Val Asn Ala Leu Asn Ser Pro Leu His Gln Glu Tyr Glu Glu Asn
                20                  25                  30

Leu Gly Asp Ser Ile Val Gly Tyr Lys Glu Lys Ser Lys Phe Gln Asp
            35                  40                  45

Thr His Asn Asn Ala His Tyr Tyr Val Phe Phe Glu Glu Gln Glu Asp
        50                  55                  60

Glu Ile Ile Gly Phe Asn Glu Thr Leu Lys Asn Pro Gln Glu Glu Thr
65                  70                  75                  80

Leu Gln Ala Phe Asp Ser His Tyr Asp Tyr Thr Ile Cys Gly Asp Ser
                85                  90                  95

Glu Asp Met Val Cys Thr Pro Lys Ser Asp Glu Phe Asn Pro Cys Glu
            100                 105                 110

Asp Ile Met Gly Tyr Lys Phe Leu Arg
        115                 120

<210> SEQ ID NO 10
<211> LENGTH: 121
<212> TYPE: PRT
<213> ORGANISM: Artificial Sequence
<220> FEATURE:
<223> OTHER INFORMATION: Description of Artificial Sequence:This is a
      mutated TSHR.  TSHR-AAAA310-313-NET.

<400> SEQUENCE: 10

Ser Leu Met Cys Asn Glu Ser Ser Met Gln Ser Leu Ala Ala Ala Ala
 1               5                  10                  15

Ser Val Asn Ala Leu Asn Ser Pro Leu His Gln Glu Tyr Glu Glu Asn
                20                  25                  30

Leu Gly Asp Ser Ile Val Gly Tyr Lys Glu Lys Ser Lys Phe Gln Asp
            35                  40                  45

Thr His Asn Asn Ala His Tyr Tyr Val Phe Phe Glu Glu Gln Glu Asp
        50                  55                  60

Glu Ile Ile Gly Phe Asn Glu Thr Leu Lys Asn Pro Gln Glu Glu Thr
65                  70                  75                  80

Leu Gln Ala Phe Asp Ser His Tyr Asp Tyr Thr Ile Cys Gly Asp Ser
                85                  90                  95

Glu Asp Met Val Cys Thr Pro Lys Ser Asp Glu Phe Asn Pro Cys Glu
            100                 105                 110

Asp Ile Met Gly Tyr Lys Phe Leu Arg
        115                 120

<210> SEQ ID NO 11
<211> LENGTH: 121

```
<212> TYPE: PRT
<213> ORGANISM: Artificial Sequence
<220> FEATURE:
<223> OTHER INFORMATION: Description of Artificial Sequence:This is a
      mutated TSHR.  TSHR-AAAA314-316-NET.

<400> SEQUENCE: 11

Ser Leu Met Cys Asn Glu Ser Ser Met Gln Ser Leu Arg Gln Arg Lys
 1               5                  10                  15

Ala Ala Ala Ala Leu Asn Ser Pro Leu His Gln Glu Tyr Glu Glu Asn
            20                  25                  30

Leu Gly Asp Ser Ile Val Gly Tyr Lys Glu Lys Ser Lys Phe Gln Asp
        35                  40                  45

Thr His Asn Asn Ala His Tyr Tyr Val Phe Phe Glu Glu Gln Glu Asp
    50                  55                  60

Glu Ile Ile Gly Phe Asn Glu Thr Leu Lys Asn Pro Gln Glu Glu Thr
65                  70                  75                  80

Leu Gln Ala Phe Asp Ser His Tyr Asp Tyr Thr Ile Cys Gly Asp Ser
                85                  90                  95

Glu Asp Met Val Cys Thr Pro Lys Ser Asp Glu Phe Asn Pro Cys Glu
            100                 105                 110

Asp Ile Met Gly Tyr Lys Phe Leu Arg
        115                 120

<210> SEQ ID NO 12
<211> LENGTH: 71
<212> TYPE: PRT
<213> ORGANISM: Artificial Sequence
<220> FEATURE:
<223> OTHER INFORMATION: Description of Artificial Sequence:This is a
      mutated human TSHR.  TSHR- delta-NET.

<400> SEQUENCE: 12

Ser Leu Met Cys Asn Glu Ser Ser Met Gln Ser Leu Arg Gln Arg Lys
 1               5                  10                  15

Ser Val Asn Asn Glu Thr Leu Lys Asn Pro Gln Glu Glu Thr Leu Gln
            20                  25                  30

Ala Phe Asp Ser His Tyr Asp Tyr Thr Ile Cys Gly Asp Ser Glu Asp
        35                  40                  45

Met Val Cys Thr Pro Lys Ser Asp Glu Phe Asn Pro Cys Glu Asp Ile
    50                  55                  60

Met Gly Tyr Lys Phe Leu Arg
65                  70

<210> SEQ ID NO 13
<211> LENGTH: 71
<212> TYPE: PRT
<213> ORGANISM: Artificial Sequence
<220> FEATURE:
<223> OTHER INFORMATION: Description of Artificial Sequence:This is a
      mutated TSHR.  TSHR-delta-50.

<400> SEQUENCE: 13

Ser Leu Met Cys Asn Glu Ser Ser Met Gln Ser Leu Arg Gln Arg Lys
 1               5                  10                  15

Ser Val Asn Gly Gln Glu Leu Lys Asn Pro Gln Glu Glu Thr Leu Gln
            20                  25                  30

Ala Phe Asp Ser His Tyr Asp Tyr Thr Ile Cys Gly Asp Ser Glu Asp
        35                  40                  45

Met Val Cys Thr Pro Lys Ser Asp Glu Phe Asn Pro Cys Glu Asp Ile
```

```
                    50                  55                  60
Met Gly Tyr Lys Phe Leu Arg
 65                  70
```

<210> SEQ ID NO 14
<211> LENGTH: 121
<212> TYPE: PRT
<213> ORGANISM: Artificial Sequence
<220> FEATURE:
<223> OTHER INFORMATION: Description of Artificial Sequence:This is a
      mutated THSR.  23 TSHR mutations encompassing AA
      317-362.

<400> SEQUENCE: 14

```
Ser Leu Met Cys Asn Glu Ser Ser Met Gln Ser Leu Arg Gln Arg Lys
  1               5                  10                  15

Ser Val Asn Ala Ala Ala Ala Ala Ala Ala Ala Ala Ala Glu Glu Asn
                 20                  25                  30

Leu Gly Asp Ser Ile Val Gly Tyr Lys Glu Lys Ser Lys Phe Gln Asp
             35                  40                  45

Thr His Asn Asn Ala His Tyr Tyr Val Phe Phe Glu Gln Ala Gln Ala
         50                  55                  60

Gln Ile Ile Gly Phe Gly Gln Glu Leu Lys Asn Pro Gln Glu Glu Thr
 65                  70                  75                  80

Leu Gln Ala Phe Asp Ser His Tyr Asp Tyr Thr Ile Cys Gly Asp Ser
                 85                  90                  95

Glu Asp Met Val Cys Thr Pro Lys Ser Asp Glu Phe Asn Pro Cys Glu
                100                 105                 110

Asp Ile Met Gly Tyr Lys Phe Leu Arg
            115                 120
```

<210> SEQ ID NO 15
<211> LENGTH: 50
<212> TYPE: PRT
<213> ORGANISM: human tshr
<220> FEATURE:
<223> OTHER INFORMATION: This is cleavage site 1.

<400> SEQUENCE: 15

```
Ala Leu Asn Ser Pro Leu His Gln Glu Tyr Glu Glu Asn Leu Gly Asp
  1               5                  10                  15

Ser Ile Val Gly Tyr Lys Glu Lys Ser Lys Phe Gln Asp Thr His Asn
                 20                  25                  30

Asn Ala His Tyr Tyr Val Phe Phe Glu Glu Gln Glu Asp Glu Ile Ile
             35                  40                  45

Gly Phe
     50
```

<210> SEQ ID NO 16
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 16

```
Ala Leu Asn Ser Pro Leu His Gln Glu Tyr Glu Glu Asn Ala Gly Asp
  1               5                  10                  15

Ser Ile Val Gly Tyr Lys Glu Lys Ser Lys Phe Gln Asp Thr His Asn
                 20                  25                  30
```

Asn Ala His Tyr Tyr Val Phe Phe Glu Glu Gln Glu Asp Glu Ile Ile
            35                  40                  45

Gly Phe
    50

<210> SEQ ID NO 17
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 17

Ala Leu Asn Ser Pro Leu His Gln Glu Tyr Glu Glu Asn Leu Ala Asp
 1               5                  10                  15

Ser Ile Val Gly Tyr Lys Glu Lys Ser Lys Phe Gln Asp Thr His Asn
            20                  25                  30

Asn Ala His Tyr Tyr Val Phe Phe Glu Glu Gln Glu Asp Glu Ile Ile
            35                  40                  45

Gly Phe
    50

<210> SEQ ID NO 18
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 18

Ala Leu Asn Ser Pro Leu His Gln Glu Tyr Glu Glu Asn Leu Gly Ala
 1               5                  10                  15

Ser Ile Val Gly Tyr Lys Glu Lys Ser Lys Phe Gln Asp Thr His Asn
            20                  25                  30

Asn Ala His Tyr Tyr Val Phe Phe Glu Glu Gln Glu Asp Glu Ile Ile
            35                  40                  45

Gly Phe
    50

<210> SEQ ID NO 19
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 19

Ala Leu Asn Ser Pro Leu His Gln Glu Tyr Glu Glu Asn Leu Gly Asp
 1               5                  10                  15

Ala Ile Val Gly Tyr Lys Glu Lys Ser Lys Phe Gln Asp Thr His Asn
            20                  25                  30

Asn Ala His Tyr Tyr Val Phe Phe Glu Glu Gln Glu Asp Glu Ile Ile
            35                  40                  45

Gly Phe
    50

<210> SEQ ID NO 20
<211> LENGTH: 50

```
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 20

Ala Leu Asn Ser Pro Leu His Gln Glu Tyr Glu Glu Asn Leu Gly Asp
  1               5                  10                  15

Ser Ile Val Gly Tyr Lys Glu Lys Ser Lys Phe Gln Asp Thr His Asn
                 20                  25                  30

Asn Ala His Tyr Tyr Val Phe Phe Glu Glu Gln Glu Asp Glu Ile Ile
             35                  40                  45

Gly Phe
     50

<210> SEQ ID NO 21
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 21

Ala Leu Asn Ser Pro Leu His Gln Glu Tyr Glu Glu Asn Leu Gly Asp
  1               5                  10                  15

Ser Ile Ala Gly Tyr Lys Glu Lys Ser Lys Phe Gln Asp Thr His Asn
                 20                  25                  30

Asn Ala His Tyr Tyr Val Phe Phe Glu Glu Gln Glu Asp Glu Ile Ile
             35                  40                  45

Gly Phe
     50

<210> SEQ ID NO 22
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 22

Ala Leu Asn Ser Pro Leu His Gln Glu Tyr Glu Glu Asn Leu Gly Asp
  1               5                  10                  15

Ser Ile Val Gly Tyr Lys Glu Lys Ser Lys Phe Gln Asp Thr His Asn
                 20                  25                  30

Asn Ala His Tyr Tyr Val Phe Phe Glu Glu Gln Glu Asp Glu Ile Ile
             35                  40                  45

Gly Phe
     50

<210> SEQ ID NO 23
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 23

Ala Leu Asn Ser Pro Leu His Gln Glu Tyr Glu Glu Asn Leu Gly Asp
  1               5                  10                  15
```

-continued

Ser Ile Val Gly Ala Lys Glu Lys Ser Lys Phe Gln Asp Thr His Asn
            20                  25                  30

Asn Ala His Tyr Tyr Val Phe Phe Glu Glu Gln Glu Asp Glu Ile Ile
        35                  40                  45

Gly Phe
    50

<210> SEQ ID NO 24
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 24

Ala Leu Asn Ser Pro Leu His Gln Glu Tyr Glu Glu Asn Leu Gly Asp
 1               5                  10                  15

Ser Ile Val Gly Tyr Ala Glu Lys Ser Lys Phe Gln Asp Thr His Asn
            20                  25                  30

Asn Ala His Tyr Tyr Val Phe Phe Glu Glu Gln Glu Asp Glu Ile Ile
        35                  40                  45

Gly Phe
    50

<210> SEQ ID NO 25
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 25

Gly Ala Ala Ala Pro Leu His Gln Glu Tyr Glu Glu Asn Leu Gly Asp
 1               5                  10                  15

Ser Ile Val Gly Tyr Lys Glu Lys Ser Lys Phe Gln Asp Thr His Asn
            20                  25                  30

Asn Ala His Tyr Tyr Val Phe Phe Glu Glu Gln Glu Asp Glu Ile Ile
        35                  40                  45

Gly Phe
    50

<210> SEQ ID NO 26
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 26

Ala Leu Asn Ser Ala Ala Ala Gln Glu Tyr Glu Glu Asn Leu Gly Asp
 1               5                  10                  15

Ser Ile Val Gly Tyr Lys Glu Lys Ser Lys Phe Gln Asp Thr His Asn
            20                  25                  30

Asn Ala His Tyr Tyr Val Phe Phe Glu Glu Gln Glu Asp Glu Ile Ile
        35                  40                  45

Gly Phe
    50

<210> SEQ ID NO 27
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 27

Ala Leu Asn Ser Pro Leu His Ala Ala Glu Glu Asn Leu Gly Asp
 1               5                  10                  15

Ser Ile Val Gly Tyr Lys Glu Lys Ser Lys Phe Gln Asp Thr His Asn
                20                  25                  30

Asn Ala His Tyr Tyr Val Phe Phe Glu Glu Gln Glu Asp Glu Ile Ile
            35                  40                  45

Gly Phe
     50

<210> SEQ ID NO 28
<211> LENGTH: 50
<212> TYPE: PRT
<213> ORGANISM: Artificial Sequence
<220> FEATURE:
<223> OTHER INFORMATION: Description of Artificial Sequence:This is
      mutated cleavage site 1 of TSHR.

<400> SEQUENCE: 28

Ala Leu Asn Ser Pro Leu His Gln Glu Tyr Ala Ala Ala Leu Gly Asp
 1               5                  10                  15

Ser Ile Val Gly Tyr Lys Glu Lys Ser Lys Phe Gln Asp Thr His Asn
                20                  25                  30

Asn Ala His Tyr Tyr Val Phe Phe Glu Glu Gln Glu Asp Glu Ile Ile
            35                  40                  45

Gly Phe
     50

<210> SEQ ID NO 29
<211> LENGTH: 50
<212> TYPE: PRT
<213> ORGANISM: Artificial Sequence
<220> FEATURE:
<223> OTHER INFORMATION: Description of Artificial Sequence: This is a
      mutated cleavage site of TSHR.

<400> SEQUENCE: 29

Ala Leu Asn Ser Pro Leu His Gln Glu Tyr Glu Glu Asn Ala Ala Ala
 1               5                  10                  15

Ala Ile Val Gly Tyr Lys Glu Lys Ser Lys Phe Gln Asp Thr His Asn
                20                  25                  30

Asn Ala His Tyr Tyr Val Phe Phe Glu Glu Gln Glu Asp Glu Ile Ile
            35                  40                  45

Gly Phe
     50

<210> SEQ ID NO 30
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 30

```
Ala Leu Asn Ser Pro Leu His Gln Glu Tyr Glu Glu Asn Leu Gly Asp
  1               5                  10                  15

Ser Ala Ala Ala Tyr Lys Glu Lys Ser Lys Phe Gln Asp Thr His Asn
             20                  25                  30

Asn Ala His Tyr Tyr Val Phe Phe Glu Glu Gln Glu Asp Glu Ile Ile
         35                  40                  45

Gly Phe
     50

<210> SEQ ID NO 31
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of the THSR.

<400> SEQUENCE: 31

Ala Leu Asn Ser Pro Leu His Gln Glu Tyr Glu Glu Asn Leu Gly Asp
  1               5                  10                  15

Ser Ile Val Gly Tyr Lys Ala Ala Lys Phe Gln Asp Thr His Asn
             20                  25                  30

Gly Phe
    50

<210> SEQ ID NO 34
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 34

Ala Leu Asn Ser Pro Leu His Gln Glu Tyr Glu Glu Asn Leu Gly Asp
 1               5                  10                  15

Ser Ile Val Gly Tyr Lys Glu Lys Ser Lys Phe Gln Asp Thr His Asn
            20                  25                  30

Ala Ala Ala Ala Tyr Val Phe Phe Glu Glu Gln Glu Asp Glu Ile Ile
        35                  40                  45

Gly Phe
    50

<210> SEQ ID NO 35
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 35

Ala Leu Asn Ser Pro Leu His Gln Glu Tyr Glu Glu Asn Leu Gly Asp
 1               5                  10                  15

Ser Ile Val Gly Tyr Lys Glu Lys Ser Lys Phe Gln Asp Thr His Asn
            20                  25                  30

Asn Ala His Tyr Ala Ala Ala Ala Gln Glu Gln Glu Asp Glu Ile Ile
        35                  40                  45

Gly Phe
    50

<210> SEQ ID NO 36
<211> LENGTH: 50
<212> TYPE: PRT
<213> ORGANISM: Artificial Sequence
<220> FEATURE:
<223> OTHER INFORMATION: Description of Artificial Sequence:This is a
      mutated cleavage site 1 of TSHR.

<400> SEQUENCE: 36

Ala Leu Asn Ser Pro Leu His Gln Glu Tyr Glu Glu Asn Leu Gly Asp
 1               5                  10                  15

Ser Ile Val Gly Tyr Lys Glu Lys Ser Lys Phe Gln Asp Thr His Asn
            20                  25                  30

Asn Ala His Tyr Tyr Val Phe Phe Glu Gln Ala Gln Asn Gln Ile Ile
        35                  40                  45

Gly Phe
    50

<210> SEQ ID NO 37
<211> LENGTH: 51
<212> TYPE: PRT
<213> ORGANISM: Unknown Organism
<220> FEATURE:
<223> OTHER INFORMATION: Description of Unknown Organism:This may be a -continued

```
      fragment of a LH/CG receptor from a human.  This
      fragment is the cleavage site 2 of the LH/CG
      receptor.
<223> OTHER INFORMATION: There may be one or more amino insertion
      between the cysteine at position 24 and serine at position
      25.

<400> SEQUENCE: 37

Asn Glu Thr Leu Tyr Ser Ala Ile Phe Glu Asn Glu Leu Ser Gly
 1               5                  10                  15

Trp Asp Tyr Asp Tyr Gly Phe Cys Ser Pro Lys Thr Leu Gln Cys Ala
                20                  25                  30

Pro Glu Pro Asp Ala Phe Asn Pro Cys Glu Asp Ile Met Gly Tyr Ala
            35                  40                  45

Phe Leu Pro
        50

<210> SEQ ID NO 38
<211> LENGTH: 52
<212> TYPE: PRT
<213> ORGANISM: Unknown Organism
<220> FEATURE:
<223> OTHER INFORMATION: Description of Unknown Organism:This may be a
      cleavage site 2 of a human TSHR.

<400> SEQUENCE: 38

Gly Gln Glu Leu Lys Asn Pro Gln Glu Glu Thr Leu Gln Ala Phe Asp
 1               5                  10                  15

Ser His Tyr Asp Tyr Thr Ile Cys Gly Asp Ser Glu Asp Met Val Cys
                20                  25                  30

Thr Pro Lys Ser Asp Glu Phe Asn Pro Cys Glu Asp Ile Met Gly Tyr
            35                  40                  45

Lys Phe Leu Arg
        50

<210> SEQ ID NO 39
<211> LENGTH: 52
<212> TYPE: PRT
<213> ORGANISM: Artificial Sequence
<220> FEATURE:
<223> OTHER INFORMATION: Description of Artificial Sequence: This is a
      mutated cleavage site 2 of TSHR.

<400> SEQUENCE: 39

Asn Glu Thr Leu Tyr Ser Ala Ile Phe Glu Thr Leu Gln Ala Phe Asp
 1               5                  10                  15

Ser His Tyr Asp Tyr Thr Ile Cys Gly Asp Ser Glu Asp Met Val Cys
                20                  25                  30

Thr Pro Lys Ser Asp Glu Phe Asn Pro Cys Glu Asp Ile Met Gly Tyr
            35                  40                  45

Lys Phe Leu Arg
        50

<210> SEQ ID NO 40
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 40

Gly Gln Glu Leu Lys Asn Pro Gln Glu Glu Glu Asn Glu Leu Ser Gly
```

```
            1               5                  10                 15
Trp Asp Tyr Asp Tyr Thr Ile Cys Gly Asp Ser Glu Asp Met Val Cys
                    20                  25                  30

Thr Pro Lys Ser Asp Glu Phe Asn Pro Cys Glu Asp Ile Met Gly Tyr
        35                  40                  45

Lys Phe Leu Arg
    50

<210> SEQ ID NO 41
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 41

Gly Gln Glu Leu Lys Asn Pro Gln Glu Glu Thr Leu Gln Ala Phe Asp
  1               5                  10                 15

Ser His Tyr Asp Tyr Gly Phe Cys Ser Pro Lys Thr Leu Met Val Cys
                    20                  25                  30

Thr Pro Lys Ser Asp Glu Phe Asn Pro Cys Glu Asp Ile Met Gly Tyr
        35                  40                  45

Lys Phe Leu Arg
    50

<210> SEQ ID NO 42
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 42

Asn Glu Thr Leu Tyr Asn Pro Gln Glu Glu Thr Leu Gln Ala Phe Asp
  1               5                  10                 15

Ser His Tyr Asp Tyr Thr Ile Cys Gly Asp Ser Glu Asp Met Val Cys
                    20                  25                  30

Thr Pro Lys Ser Asp Glu Phe Asn Pro Cys Glu Asp Ile Met Gly Tyr
        35                  40                  45

Lys Phe Leu Arg
    50

<210> SEQ ID NO 43
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 43

Gly Gln Glu Leu Lys Asn Pro Gln Glu Glu Thr Leu Gln Ala Phe Asp
  1               5                  10                 15

Ser His Tyr Asp Tyr Thr Ile Cys Gly Asp Ser Glu Asp Met Val Cys
                    20                  25                  30

Thr Pro Lys Ser Asp Glu Phe Asn Pro Cys Glu Asp Ile Met Gly Tyr
        35                  40                  45

Lys Phe Leu Arg
    50
```

<210> SEQ ID NO 44
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 44

Ala Gln Glu Leu Lys Asn Pro Gln Glu Thr Leu Gln Ala Phe Asp
 1               5                  10                  15

Ser His Tyr Asp Tyr Thr Ile Cys Gly Asp Ser Glu Asp Met Val Cys
                20                  25                  30

Thr Pro Lys Ser Asp Glu Phe Asn Pro Cys Glu Asp Ile Met Gly Tyr
            35                  40                  45

Lys Phe Leu Arg
        50

<210> SEQ ID NO 45
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 45

Gly Ala Glu Leu Lys Asn Pro Gln Glu Thr Leu Gln Ala Phe Asp
 1               5                  10                  15

Ser His Tyr Asp Tyr Thr Ile Cys Gly Asp Ser Glu Asp Met Val Cys
                20                  25                  30

Thr Pro Lys Ser Asp Glu Phe Asn Pro Cys Glu Asp Ile Met Gly Tyr
            35                  40                  45

Lys Phe Leu Arg
        50

<210> SEQ ID NO 46
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 46

Gly Gln Ala Leu Lys Asn Pro Gln Glu Thr Leu Gln Ala Phe Asp
 1               5                  10                  15

Ser His Tyr Asp Tyr Thr Ile Cys Gly Asp Ser Glu Asp Met Val Cys
                20                  25                  30

Thr Pro Lys Ser Asp Glu Phe Asn Pro Cys Glu Asp Ile Met Gly Tyr
            35                  40                  45

<400> SEQUENCE: 47

Gly Gln Glu Leu Ala Asn Pro Gln Glu Glu Thr Leu Gln Ala Phe Asp
 1               5                  10                  15

Ser His Tyr Asp Tyr Thr Ile Cys Gly Asp Ser Glu Asp Met Val Cys
                20                  25                  30

Thr Pro Lys Ser Asp Glu Phe Asn Pro Cys Glu Asp Ile Met Gly Tyr
        35                  40                  45

Lys Phe Leu Arg
        50

<210> SEQ ID NO 48
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 48

Asn Glu Thr Leu Lys Asn Pro Gln Glu Glu Thr Leu Gln Ala Phe Asp
 1               5                  10                  15

Ser His Tyr Asp Tyr Thr Ile Cys Gly Asp Ser Glu Asp Met Val Cys
                20                  25                  30

Thr Pro Lys Ser Asp Glu Phe Asn Pro Cys Glu Asp Ile Met Gly Tyr
        35                  40                  45

Lys Phe Leu Arg
        50

<210> SEQ ID NO 49
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 49

Gly Gln Thr Leu Tyr Asn Pro Gln Glu Glu Thr Leu Gln Ala Phe Asp
 1               5                  10                  15

Ser His Tyr Asp Tyr Thr Ile Cys Gly Asp Ser Glu Asp Met Val Cys
                20                  25                  30

Thr Pro Lys Ser Asp Glu Phe Asn Pro Cys Glu Asp Ile Met Gly Tyr
        35                  40                  45

Lys Phe Leu Arg
        50

<210> SEQ ID NO 50
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 50

Ala Ala Ala Leu Lys Asn Pro Gln Glu Glu Thr Leu Gln Ala Phe Asp
 1               5                  10                  15

Ser His Tyr Asp Tyr Thr Ile Cys Gly Asp Ser Glu Asp Met Val Cys
20 25 30

Thr Pro Lys Ser Asp Glu Phe Asn Pro Cys Glu Asp Ile Met Gly Tyr
35 40 45

Lys Phe Leu Arg
    50

<210> SEQ ID NO 51
<211> LENGTH: 52
<212> TYPE: PRT
<213> ORGANISM: Artificial Sequence
<220> FEATURE:
<223> OTHER INFORMATION: Description of Artificial Sequence:This is
      mutated cleavage site 2 of TSHR.

<400> SEQUENCE: 51

Asn Gln Glu Leu Lys Asn Pro Gln Glu Glu Thr Leu Gln Ala Phe Asp
 1               5                  10                  15

Ser His Tyr Asp Tyr Thr Ile Cys Gly Asp Ser Glu Asp Met Val Cys
            20                  25                  30

Thr Pro Lys Ser Asp Glu Phe Asn Pro Cys Glu Asp Ile Met Gly Tyr
        35                  40                  45

Lys Phe Leu Arg
    50

<210> SEQ ID NO 52
<211> LENGTH: 52
<212> TYPE: PRT
<213> ORGANISM: Artificial Sequence
<220> FEATURE:
<223> OTHER INFORMATION: Description of Artificial Sequence:This is a
      mutated cleavage site 2 of TSHR.

<400> SEQUENCE: 52

Asn Gln Thr Leu Lys Asn Pro Gln Glu Glu Thr Leu Gln Ala Phe Asp
 1               5                  10                  15

Ser His Tyr Asp Tyr Thr Ile Cys Gly Asp Ser Glu Asp Met Val Cys
            20                  25                  30

Thr Pro Lys Ser Asp Glu Phe Asn Pro Cys Glu Asp Ile Met Gly Tyr
        35                  40                  45

Lys Phe Leu Arg
    50

<210> SEQ ID NO 53
<211> LENGTH: 764
<212> TYPE: PRT
<213> ORGANISM: human tshr

<400> SEQUENCE: 53

Met Arg Pro Ala Asp Leu Leu Gln Leu Val Leu Leu Leu Asp Leu Pro
 1               5                  10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

```
Asn Leu Thr Tyr Ile Asp Phe Asp Ala Leu Lys Ile Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Ile Asp
145                 150                 155                 160

Asn Pro Tyr Asn Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Met Phe Ser
    290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser Asn
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Leu Ile Leu Leu Thr Ser His Tyr Lys Leu Asn Val
        435                 440                 445

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Cys Ala Ile Met Val Gly
```

| | | | | | | | | | | | | | | |
|---|---|---|---|---|---|---|---|---|---|---|---|---|---|---|
| | | 530 | | | | 535 | | | | 540 | | | | |
| Gly | Trp | Val | Cys | Cys | Pro | Leu | Leu | Ala | Leu | Leu | Pro | Leu | Val | Gly | Ile |
| 545 | | | | | 550 | | | | | 555 | | | | | 560 |
| Ser | Ser | Tyr | Ala | Lys | Val | Ser | Ile | Cys | Leu | Pro | Met | Asp | Thr | Glu | Thr |
| | | | | 565 | | | | | 570 | | | | | 575 | |
| Pro | Leu | Ala | Leu | Ala | Tyr | Ile | Val | Phe | Val | Leu | Thr | Leu | Asn | Ile | Val |
| | | | 580 | | | | | 585 | | | | | 590 | | |
| Ala | Phe | Val | Ile | Val | Cys | Cys | Cys | His | Val | Lys | Ile | Tyr | Ile | Thr | Val |
| | | 595 | | | | | 600 | | | | | 605 | | | |
| Arg | Asn | Pro | Gln | Tyr | Asn | Pro | Gly | Asp | Lys | Asp | Thr | Lys | Ile | Ala | Lys |
| | 610 | | | | | 615 | | | | | 620 | | | | |
| Arg | Met | Ala | Val | Leu | Ile | Phe | Thr | Asp | Phe | Ile | Cys | Met | Ala | Pro | Ile |
| 625 | | | | | 630 | | | | | 635 | | | | | 640 |
| Ser | Phe | Tyr | Ala | Leu | Ser | Ala | Ile | Leu | Asn | Lys | Pro | Leu | Ile | Thr | Val |
| | | | | 645 | | | | | 650 | | | | | 655 | |
| Ser | Asn | Ser | Lys | Ile | Leu | Leu | Val | Leu | Phe | Tyr | Pro | Leu | Asn | Ser | Lys |
| | | | 660 | | | | | 665 | | | | | 670 | | |
| Ala | Asn | Pro | Phe | Leu | Tyr | Ala | Ile | Phe | Thr | Lys | Ala | Phe | Gln | Arg | Asp |
| | | 675 | | | | | 680 | | | | | 685 | | | |
| Val | Phe | Ile | Leu | Leu | Ser | Arg | Phe | Gly | Ile | Cys | Lys | Arg | Gln | Ala | Gln |
| | 690 | | | | | 695 | | | | | 700 | | | | |
| Ala | Thr | Arg | Gly | Gln | Arg | Val | Pro | Pro | Lys | Asn | Ser | Thr | Asp | Ile | Gln |
| 705 | | | | | 710 | | | | | 715 | | | | | 720 |
| Val | Gln | Lys | Val | Thr | His | Asp | Met | Arg | Gln | Gly | Leu | His | Asn | Met | Glu |
| | | | | 725 | | | | | 730 | | | | | 735 | |
| Asp | Val | Tyr | Glu | Leu | Ile | Glu | Asn | Ser | Asn | Leu | Thr | Pro | Lys | Lys | Gln |
| | | | 740 | | | | | 745 | | | | | 750 | | |
| Gly | Gln | Ile | Ser | Glu | Glu | Tyr | Met | Gln | Thr | Val | Leu | | | | |
| | | | 755 | | | | | 760 | | | | | | | |

<210> SEQ ID NO 54
<211> LENGTH: 2469
<212> TYPE: DNA
<213> ORGANISM: human tshr

<400> SEQUENCE: 54

```
ccgctcccgg gtctcctttc ccctggccta acccgaggtg cagagctgag aatgaggcga      60
tttcggagga tggagaaata gccccgagtc ccgtggaaaa tgaggccggc ggacttgctg     120
cagctggtgc tgctgctcga cctgcccagg gacctgggcg gaatggggtc ttcgtctcca     180
ccctgcgagt gccatcagga ggaggacttc agagtcacct gcaaggatat tcaacgcatc     240
cccagcttac cgcccagtac gcagactctg aagcttattg agactcacct gagaactatt     300
ccaagtcatg cattttctaa tctgcccaat atttccagaa tctacgtatc tatagatgtg     360
actctgcagc agctggaatc acactccttc tacaatttga gtaaagtgac tcacatagaa     420
attcggaata ccaggaactt aacttacata gaccctgatg ccctcaaaga gctccccctc     480
ctaaagttcc ttggcatttt caacactgga cttaaaatgt tccctgacct gaccaaagtt     540
tattccactg atatattctt tatacttgaa attacagaca accttacat gacgtaaatc     600
cctgtgaatg cttttcaggg actatgcaat gaaaccttga cactgaagct gtacaacaat     660
ggctttactt cagtccaagg atatgctttc aatgggacaa agctggatgc tgtttaccta     720
aacaagaata aatacctgac agttattgac aaagatgcat tggaggagt atacagtgga     780
ccaagcttgc tggacgtgtc tcaaaccagt gtcactgccc ttccatccaa aggcctggag     840
```

```
cacctgaagg aactgatagc aagaaacacc tggactctta agaaacttcc actttccttg      900
agtttccttc acctcacacg ggctgacctt tcttacccaa gccactgctg tgcttttaag      960
aatcagaaga aaatcagagg aatccttgag tccttgatgt gtaatgagag cagtatgcag     1020
agcttgcgcc agagaaaatc tgtgaatgcc ttgaatagcc ccctccacca ggaatatgaa     1080
gagaatctgg gtgacagcat tgttgggtac aaggaaaagt ccaagttcca ggatactcat     1140
aacaacgctc attattacgt cttctttgaa gaacaagagg atgagatcat tggttttggc     1200
caggagctca aaaaccccca gcaagagact ctacaagctt tgacagcca ttatgactac      1260
accatatgtg gggacagtga agacatggtg tgtaccccca agtccgatga gttcaacccg     1320
tgtgaagaca taatgggcta caagttcctg agaattgtgg tgtggttcgt tagtctgctg     1380
gctctcctgg gcaatgtctt tgtcctgctt attctcctca ccagccacta caaactgaac     1440
gtcccccgct ttctcatgtg caacctgcc tttgcggatt tctgcatggg gatgtacctg      1500
ctcctcatcg cctctgtaga cctctacact cactctgagt actacaacca tgccatcgac     1560
tggcagacag gccctgggtg caacacggct ggtttcttca ctgtctttgc aagcgagtta     1620
tcggtgtata cgctgacggt catcaccctg gagcgctggt atgccatcac cttcgccatg     1680
cgcctggacc ggaagatccg cctcaggcac gcatgtgcca tcatggttgg gggctgggtt     1740
tgctgcttcc ttctcgccct gcttcctttg gtgggaataa gtagctatgc caaagtcagt     1800
atctgcctgc ccatggacac cgagacccct cttgctctgg catatattgt ttttgttctg     1860
acgctcaaca tagttgcctt cgtcatcgtc tgctgctgtc atgtgaagat ctacatcaca     1920
gtccgaaatc cgcagtacaa cccaggggac aaagatacca aaattgccaa gaggatggct     1980
gtgttgatct tcaccgactt catatgcatc gccccaatct cattctatgc tctgtcagca     2040
attctgaaca agcctctcat cactgttagc aactccaaaa tcttgctggt actcttctat     2100
ccacttaact cctgtgccaa tccattcctc tatgctattt tcaccaaggc cttccagagg     2160
gatgtgttca tcctactcag caagtttggc atctgtaaac gccaggctca ggcataccgg     2220
gggcagaggg ttcctccaaa gaacagcact gatattcagg ttcaaaaggt tacccacgac     2280
atgaggcagg gtctccacaa catggaacat gtctatgaac tgattgaaaa ctcccatcta     2340
accccaaaga accaaggcca aatctcagaa gagtatatgc aaacggtttt gtaagttaac     2400
actacactac tcacaatggt aggggaactt acaaaataat agtttcttga atatgcattc     2460
caatcccat                                                             2469
```

NUCLEIC ACID ENCODING HUMAN THYROTROPIN RECEPTOR

CROSS REFERENCE TO RELATED APPLICATION

This application claims the benefit of U.S. Provisional Application No. 60/064,287 filed Nov. 5, 1997.

FUNDING

Support for this invention may have included Government support under Grants, and as such the Government has certain rights in the invention.

FIELD OF THE INVENTION

The present invention relates to the field of molecular biology and immunology. More particularly, the invention relates to human thyrotropin receptor compositions. The invention is also related to diagnostic and therapeutic applications using human thyrotropin receptor compositions according to the present invention.

BACKGROUND OF THE INVENTION

The most important of the diseases that cause thyrotoxicosis is Graves' disease, also known as Parry's or Basdow's disease. However, not all hyperthyroidism is a result of Grave's disease. Additionally, not all thyrotoxicosis is due to hyperthyroidism. Thyrotoxicosis is the clinical, biochemical and physiological result of sustained delivery of excessive quantities of thyroid hormones to the peripheral tissues. Hyperthyroidism is used to denote the situation where excess thyroid hormones stems from sustained thyroid hyperfunction.

There are a number of causes for thyrotoxicosis, the major ones include: Graves' disease, toxic adenoma, toxic multi-nodular goiter, thyrotoxicosis factitia, ectopic thyroid, and thyroiditis. A portion of these are hyperthyroid based whereas the remaining portion is nonhyperthyroid. Graves' disease is by far the most common cause of thyrotoxicosis, as well as the only autoimmune cause, it is therefore of extreme importance that an accurate assay be available to allow the differentiation between the auto immune and non-autoimmune varieties since the treatments, and pathogenesis differ so drastically. Bardin, *Current Therapy in Endocrinology and Metabolism*, B. C. Decker Inc. Toronto (1988).

Graves' disease is a relatively common disorder that occurs at any age, but most often in the third and fourth decades. The disease is more frequent in women and the ratio of predominance in women may be as high as 7:1. The manifestations of Graves' disease include one or more of the following: hyperthyroidism with diffuse goiter, ophthalmopathy, and dermopathy.

Thyrotropin, also known as thyroid stimulating hormone (TSH), is the primary hormone that regulates thyroid cell differentiated function and proliferation (Dumont et al., Adv. Cyclic Nucleotide Res. 14:479–489 (1981)). These effects are mediated by its interaction with the thyrotropin (TSH) receptor on the plasma membrane of thyroid cells. Thyroid stimulating auto-antibodies, the cause of thyrotoxicosis in Graves' disease, mimic the actions of TSH by their interaction with the TSH receptor (Rees Smith et al., Endocr. Rev. 9:106–121 (1988)). In Graves' disease, anti-TSH receptor auto-antibodies bind to the TSH receptor on the thyroid cell surface. Such binding causes unregulated stimulation of the thyroid cell which then produces excessive amounts of thyroid hormone.

The pathophysiological importance of the TSH receptor has motivated efforts directed to its characterization at both the protein as well as the genetic level. Hence, it has been found that it is a member of the G-protein-coupled receptor superfamily with glycoprotein hormone ligands, and that it is characterized by large, heavily glycosilated ectodomains with leucine-rich repeats encoded by several exons. (Gross et al., Biochem. Biophys. Res. Comm. 177:679–687 (1992); Tsai-Morris et al. J. Biol. Chem. 266:11355–11359 (1991); Koo et al., Endocrinol. 128:2297–2308 (1991)). Furthermore, characterization of cell bound TSH has identified two distinct functional forms. In one form, TSH is a single peptide receptor. In a second form, TSH is a heterodimer protein complex comprising subunit peptides A and B linked by disulfide bonds (Furmaniak et al., FEBS Letters 215:316–322 (1987), and Russo et al., Mol. Endocrinology 5:1607–1612 (1991)). Immunoprecipitation or immunoblotting analysis of mammalian cell extracts have shown variable proportions of single and two subunits forms, albeit the pathological significance of this finding is yet to be understood (Lossfelt et al., Proc. Natl. Acad. Sci. USA 895:3765–3769 (1992); Hata et al., Biochem. Biophys. Res. Comm. 164:1268–1273 (1989); Potter et al., BBRC 205:361–367 (1994); Chazenbalk et al., Endocrinology 137:4586–4591 (1996); Graves et al., Endocrinology 137:3915–3920 (1996)). Recent studies have suggested that subunits A and B are the product of intramolecular cleavage at two separate sites, with the concomitant loss of a TSH fragment, referred to in the literature as peptide C (expected to correspond to an approximately 5 KDa plypeptide fragment) (Chazenbalk, et al., Endocrinology 138:2893–2899 (1997)). To date however, the sites of cleavage, the kinetics of the cleavage as well as the enzyme(s) involved have yet to be elucidated. In addition, the physiological and/or pathological implications of peptide C, if any, have yet to be investigated.

The difficulties encountered in characterizing Graves' disease at the molecular level parallel the obstacles encountered in devising sensitive and specific diagnostic assays. Thyroid stimulating auto-antibodies, originally named "long-acting thyroid stimulators" or LATS, were measured with a bioassay system (McKensie) using mouse thyroid tissue. This assay was considered to be fairly specific for Graves' disease, although positive results were found in a few patients with Hashimoto's disease and occasionally, albeit in smaller titers, in other unrelated conditions. In addition, this assay could only detect 40–45% of patients with Graves' disease. Notably, there was no correlation between titer and the severity of the disease.

More recently, other related IgG antibodies were found that prevent adsorption of LATS onto human thyroid tissue and as a group were therefore called "LATS protector." This abnormal IgG antibody (or antibodies) could be demonstrated by three different assay techniques. One technique used high-titer LATS antibody as the indicator system whose endpoint was to show that antibody in patient serum blocked uptake of the LATS antibody by human thyroid tissue. A second technique, also known as "TSH-binding inhibiting immunoglobulin" or TBII assay, measured the ability of patient antibody to inhibit or block the binding of radiolabeled TSH to human or animal thyroid acinar cell membranes. A third technique measured the ability of the antibody to stimulate human or animal thyroid acinar cell membrane-bound adenylate cyclase, producing increased cyclic adenosine monophosphate (AMP) activity. The original assay method used human thyroid tissue, so the antibody was originally called "human thyroid-stimulating immunoglobulin." Since animal thyroid tissue can be used, the assay now is simply called "thyroid-stimulating immunoglobulin" (TSI). For example, one modification of the TSI uses special TSH-dependent FRTL-5 rat tissue culture thyroid cells. The LATS-protector assay has been reported to detect that about 75%–80% (range , 60%–90%) of patients with Graves' disease. The LATS-protector assay is very complicated. The TBII technique is reported to detect only about 70%–80% (range, 39%–100%) of Graves' disease, and the TBI detects only about 75%–80% (range, 18%–100%). Neither the TBII nor the TBI are simple or easy.

In addition to the low sensitivity inherent to the systems used, most laboratories using either technique use "home-made" reagents, which accounts for much of the great variation in sensitivity reported in the literature. Furthermore, since many clinical laboratories base their test performance claims on data from one or more research laboratories using the same technique but separate reagents additional levels of variability are compounded upon standardization. Besides sensitivity, it is necessary to question specificity, since different laboratories may find different numbers of false positive results when patients with hyperfunctioning thyroid nodules, nonfunctioning nodules or goiter, thyroiditis, autoimmune disorders, and clincially normal status are tested.

At present, the TSI assay is used mainly for patients with borderline or conflicting evidence of Graves' disease, patients who have some condition that affects the results of other tests, or patients who have "isolated Graves' ophthalmopathy" (a condition in which all standard thyroid tests are normal). However, a negative test result in most laboratories does not completely exclude the diagnosis, and there is still remain a possibility of false positive results.

One of the obstacles to the development of more sensitive and specific diagnostic assays is represented by the reported instability of isolated TSH receptor preparations necessary for the assays. Instability is most likely attributable to the harsh conditions inherent to the purification process during which the A and B subunit polypeptide backbones are likely to disassociate. Thus, there remains a need for specific and sensitive assay systems.

At present, there is no therapy that can cure Grave's disease. There are several current treatments with many drawbacks. In one treatment for Graves' disease, drugs are administered that block thyroid hormone synthesis. These drugs are administered for many months or years, while waiting for a spontaneous emission of the thyroid overactivity. Another radical treatment requires ablation of part or all of the thyroid by surgery or radioactive iodine. This commonly leads to hypothyroidism and the need for life-long administration of thyroid hormone.

While there are some treatments available, none is available which is directed primarily at the underlying immunologic cause of Graves' disease. Hence, there is a need for the development of immunological approaches to the treatment and further elucidation of Graves' disease.

SUMMARY OF THE INVENTION

The invention provides novel methods and compositions for the diagnosis and treatment of Graves' disease. The present inventors have localized the two sites at which, by intramolecular cleavage, the TSH receptor A and the B subunits are formed. Thus, the invention provides compositions and methods for a convenient and economical source of recombinant TSH receptor. The invention also provides enriched TSH receptor compositions and methods of using the same. Finally, the invention provides methods for using such compositions as analytical and diagnostic tools, as potentiators of transgenic animal studies and for gene therapy approaches, and as potential therapeutic agents.

With seven transmembrane domains, the TSH receptor belongs to a family of G protein-coupled receptors, including the receptors for LH\CG, substance K, rhodopsin, serotonin, as well as the $\alpha 2$-, $\beta 1$- and $\beta 2$-adrenergic and muscarinic cholinergic receptors (McFarland et al., Science 245:494–499 (1989); Loosfelt et al., Science 245:525–528 (1989)). In contrast to the short extracellular domains recognized by the smaller ligands such as adrenergic and cholinergic agents, the extracellular domain of the TSH receptor is much larger and more complex. This finding is consistent with the complexity of the glycoprotein hormones which are approximately 30 kDa in size, and suggests that the extracellular domain plays an important role in hormone binding and signal transduction.

The identification of the cleavage sites in the TSH receptor now opens the way for future studies to answer many questions that have remained unanswered for a number of years. These questions include (a) the identification of the site(s) of binding (epitopes) of stimulatory and inhibitory anti-TSH receptor antibodies present in the sera of patients with autoimmune thyroid disease, and the relationship between these binding sites and that for TSH, (b) the determination of the mechanism of signal transaction by which TSH increases adenylate cyclase activity in thyroid cells; and (c) the mechanism by which continued TSH stimulation leads to a decrease in TSH receptor-coupling with $G_s$ and reduced adenylated cyclase activation (homologous desensitization).

The production of enriched recombinant TSH receptor preparations also makes possible new treatments for thyrotoxicosis which would not have the drawbacks of current therapies.

In a first aspect, the invention provides recombinant nucleic acid sequences in a replicatable vector encoding for the thyrotropin receptor, or a functional or chemical derivative thereof, having a deletion capable of inhibiting cleavage at site 1. In a preferred embodiment, the replicatable vector is an expression vector.

In a second aspect, the instant invention provides a recombinant thyrotropin receptor protein, or a functional or chemical derivative thereof, including a deletion capable of inhibiting cleavage at site 1. In an embodiment of the invention the deletion encompasses amino acids 317 to 366.

In a third aspect, the invention provides a recombinant nucleic acid sequence in a replicatable vector encoding for the thyrotropin receptor, or a functional or chemical derivative thereof, including a sequence encoding a cleavage-resistant moiety capable of resisting cleavage at cleavage site 2. In a preferred embodiment of this invention, the cleavage-resistant moiety is a consensus sequence for an N-linked glycosylation site.

In another embodiment of the invention, the replicatable vector is an expression vector. In yet another embodiment, the invention also provides a host cell comprising recominant DNA molecules according to the invention.

In a fourth aspect, the instant invention provides a recombinant thyrotropin receptor protein, or a functional or chemical derivative thereof, including a sequence encoding a cleavage-resistant moiety capable of resisting cleavage at cleavage site 2 in a replicatable vector.

In a preferred embodiment according to this aspect of the invention, the cleavage-resistant moiety spans residues 367 to 369. In an embodiment of the invention, the recombinant nucleic acid sequence includes both a deletion capable of inhibiting cleavage at site 1, and a sequence encoding a cleavage-resistant moiety capable of resisting cleavage at cleavage site 2 in a replicatable vector. In a preferred embodiment of the invention, the recombinant nucleic acid sequence including both a deletion capable of inhibiting cleavage at site 1, and a sequence encoding a cleavage-resistant moiety capable of resisting cleavage at cleavage site 2 is an expression vector. In yet another embodiment of the invention, the recombinant nucleic acid sequence including both a deletion capable of inhibiting cleavage at site 1, and a sequence encoding a cleavage-resistant moiety capable of resisting cleavage at cleavage site 2 is in a host cell. In another embodiment, the invention also provides a recombinant thyrotropin receptor protein including both a deletion capable of inhibiting cleavage at site 1, and a sequence encoding a cleavage-resistant moiety capable of resisting cleavage at cleavage site 2. In a most preferred embodiment, the invention provides a recombinant thyrotropin receptor protein including both a deletion corresponding to amino acids 317 to 366, capable of inhibiting cleavage at site 1, and a cleavage-resistant moiety between amino acid residues 367 to 369 capable of resisting cleavage at cleavage site 2. In another most preferred embodiment, the invention provides a recombinant thyrotropin receptor protein including both a deletion corresponding to amino acids 317 to 366, capable of inhibiting cleavage at site 1, and a consensus sequence for an N-linked glycosylation site, capable of resisting cleavage at cleavage site 2.

In a fifth aspect, the invention provides a method of producing thyrotropin receptor by culturing the transformed cell of the present invention under conditions allowing expression of thyrotropin receptor, and recovering said thyrotrophin receptor.

In a sixth aspect, the present invention provides for an antibody against the thyrotropin receptor of the invention. In an embodiment, the invention provides a method of detecting thyrotropin receptor in a sample by contacting the sample with a labeled antibody crossreactive with the thytropin receptor, so as to form a detectable complex between the thyrotropin receptor sample and the antibody. In an additional embodiment, there is provided a kit for the detection of thyrotropin receptor in a sample, including container means with one or more containers, wherein one of said containers comprises detectably labeled antibody against thyrotropin receptor.

Moreover, a method of detecting antibodies to thyrotropin receptor in a sample is provided according to the present invention, including contacting a sample with detectably labeled recombinant thyrotropin receptor, so as to form a complex between the TSH receptor antibodies in the sample and the detectably labeled recombinant TSH receptor, and detecting the complexed antibody. In an additional embodiment, there is provided a kit for the detection of antibodies to thyrotropin receptor in a sample, including container means with one or more containers. According to the embodiments, one of the containers includes detectably labeled TSH receptor.

An additional aspect of the current invention is a method for differentiating between auto immune and non-auto immune varieties of thyrotoxicosis comprising an assay specific for either thyrotropin receptor, anti-thyrotropin receptor autoantibodies or functional or chemical derivatives thereof.

Another embodiment of the current invention is a method of treating thyrotoxicosis with pharmacologically effective amounts of recombinant thyrotropin receptor, or a functional or chemical derivative thereof.

In an additional embodiment, a thymus-derived lymphocyte (T cell) is provided which is specific for the autoimmune T-cell receptor (TCR) for TSH receptor. Another embodiment of the invention provides for a pharmaceutical preparation comprising a T cell which is specific for the autoimmune TCR for TSH receptor. In yet another embodiment of the current invention, a method of treating autoimmune thyrotoxicosis is provided comprising the use of a pharmaceutical preparation comprising a T cell which is specific for the autoimmune TCR for TSH receptor.

Another embodiment provides a peptide which is specific for the autoimmune TCR for TSH receptor. Another embodiment of the invention provides for a pharmaceutical preparation comprising a peptide which is specific for the autoimmune TCR for TSH receptor. In yet another embodiment of the current invention, a method of treating autoimmune thyrotoxicosis is provided including the use of a pharmaceutical preparation comprising a peptide which is specific for the autoimmune TCR for TSH receptor.

In an additional embodiment, there is provided suppressor T cells specific for anti-thyrotropin receptor auto-antibodies. Another embodiment provides a pharmaceutical preparation including suppressor T cells specific for anti-thyrotropin receptor auto-antibodies. Yet another embodiment provides a method of treating thyrotoxicosis with a pharmaceutical preparation comprising T cells specific for anti-thyrotropin receptor auto-antibodies.

These and other non-limiting embodiments of the present invention will be apparent to those of skill from the following detailed description of the invention.

Panel B: is a representation of an autoradiograph showing radiolabeled TSH crosslinking to CHO cells stably expressing the receptors.

Figure 10A:
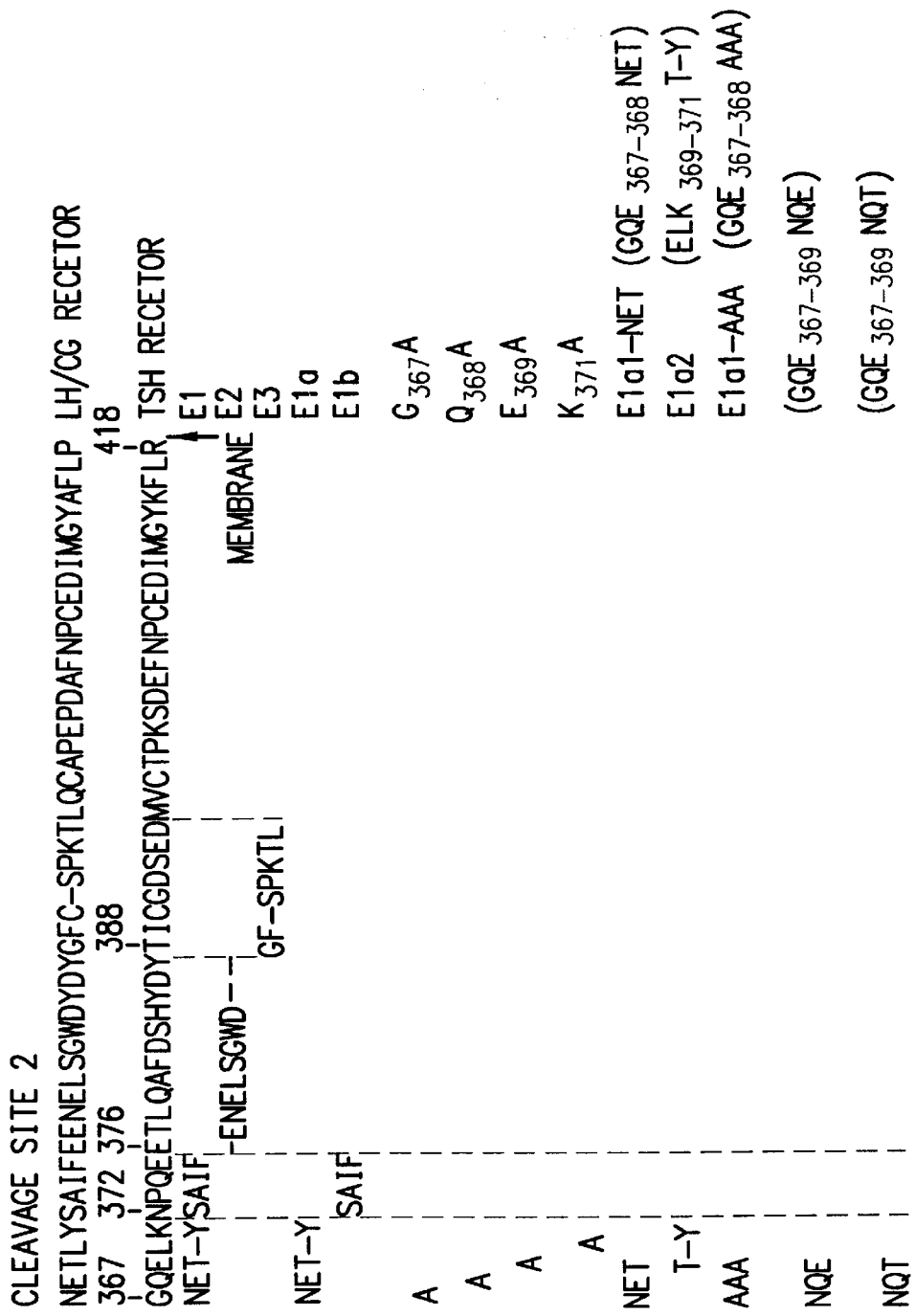
Figures 1, 10B:
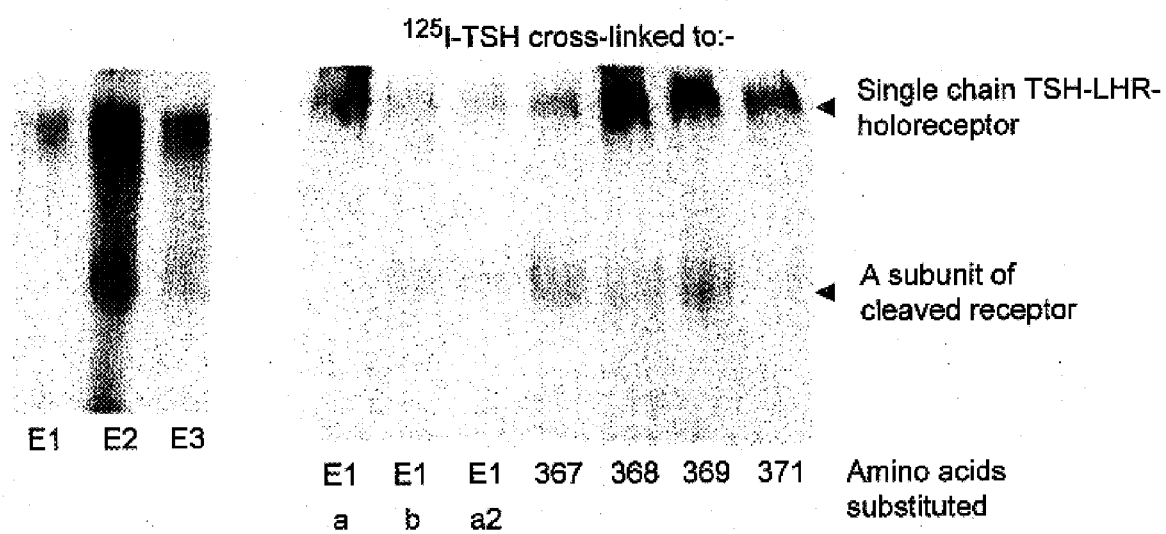
Figures 2, 10B:
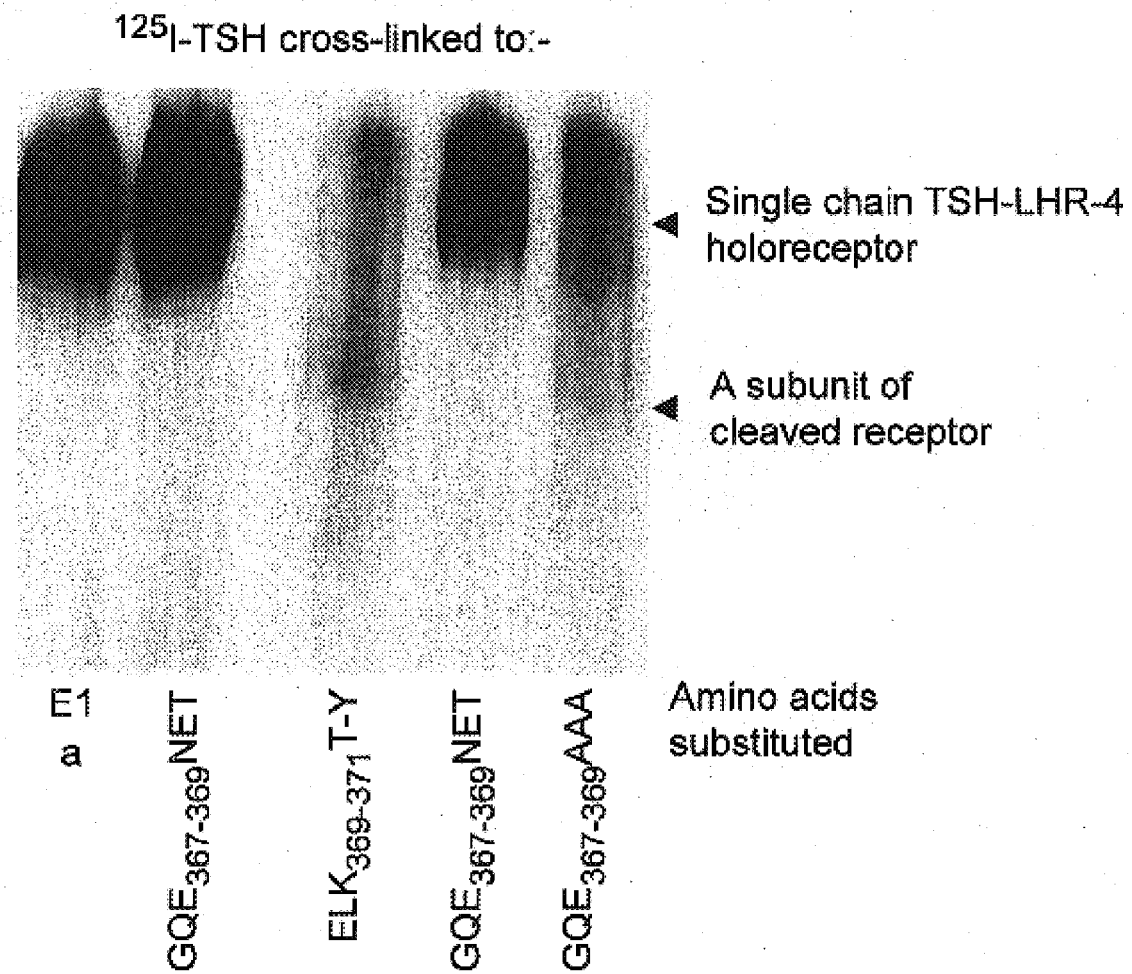

FIG. 10: Panel A: is a diagramatic representation showing amino acid substitutions introduced in the region of putative cleavage site 2 in the TSHR. Mutations were made in the E domain of chimeric receptor TSH-LHR-4. The mutations shown in bold prevent cleavage (completely, or nearly completely in the case of $GQE_{367-369}NQT$), as determined by TSH cross-linking. In the E1, E2 and E3 mutations, "-" represents no substitution because the amino acid residues are the same in both receptors. In E3, "." represents the absence of an amino acid which is not present in the LH/CG receptor.

Panel B: are autoradiographs showing radiolabeled TSH crosslinking to intact CHO cells stably expressing the receptors. Cross-linked products were reduced in order to dissociate the subunits in cleaved receptors. The upper two panels depict autoradiograms of 7.5% gels, the lower two panels show material electrophoresed in 10% gels.

Figure 11:

FIG. 11: is an autoradiograph showing that the presence of the $GQE_{367-369}NET$ mutation does not prevent cleavage of the wild-type TSHR. Cross-linked $^{125}I$-TSH-TSHR products were reduced and subjected to PAGE (10%) and autoradiography.

Figure 12A:
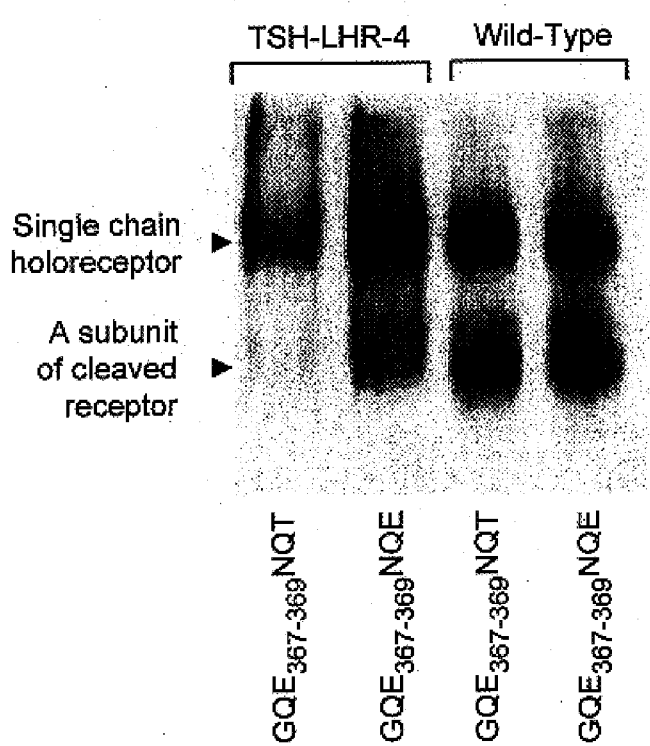
Figure 12B:
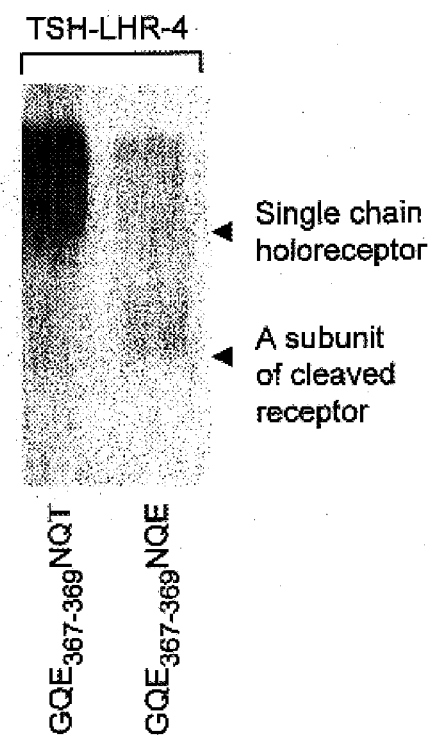

FIG. 12: is an autoradiograph showing Radiolabeled TSH crosslinking to intact CHO cells expressing receptors mutated at TSHR residues $GQE_{367-369}$ in order to explore the potential role of N-linked glycosylation in preventing cleavage at Site 2. Mutations are either in the wild-type TSHR or in chimeric receptor TSH-LHR-4 in which cleavage site 1 is eliminated. NOT would and NQE would not represent an N-linked glycosylation motif. Panel A One experiment in which inhibition of cleavage by $GQE_{367-369}NQT$ in TSH-LHR-4 is incomplete. Panel B: One of two experiments in which the $CQE_{367-369}NQT$ in TSH-LHR-4 appears to totally inhibit receptor cleavage. Cross-linked $^{125}I$-TSH-TSHR products were reduced and subjected to PAGE (7.5%) and autoradiography.

FIG. 13: is the nucleotide (SEQ ID NO: 54) and derived amino acid sequence (SEQ ID NO: 53) of the cDNA for clone 4, the human TSH receptor. Amino acids are annotated by the single letter amino acid code. Potential glycosylation sites are underlined.

DESCRIPTION OF THE PREFERRED EMBODIMENTS

In the following description, reference will be made to various methodologies known to those of skill in the art of molecular biology and immunology. Publications and other materials setting forth such known methodologies to which reference is made are incorporated herein by reference in their entireties as though set forth in full.

Standard reference works setting forth the general principles of recombinant DNA technology include Watson et al., *Molecular Biology of the Gene,* Volumes I and II, The Benjamin/Cummings Publishing Company, Inc., publisher, Menlo Park, Calif. (1987); Darnell et al., *Molecular Cell Biology,* Scientific American Books, Inc., publisher, New York, N.Y. (1986); Lewin, *Genes IV,* John Wiley & Sons, publishers, New York, N.Y. (19XX); Old et al., *Principles of Gene Manipulation: An Introduction to Genetic Engineering,* 2d edition University of California Press, publisher, Berkeley, Calif. (1981).

In a first aspect, the invention provides recombinant nucleic acid sequences in a replicable vector encoding for the throtropin receptor, or a functional or chemical derivative thereof, having a deletion capable of inhibiting cleavage at site 1. As used herein, the term "site 1" designates a site of proteolytic cleavage N-terminal to amino acid residue 317 in the Thyrotropin receptor. The term "replicatable vector" designates a nucleic acid vector able to replicate in at least one cell type. Many such replicatable vectors are well known in the art (see e.g., Sambrook et al., *Molecular Cloning: A Laboratory Manual,* Cold Spring Harbor Laboratory, publisher, Cold Spring Harbor, N.Y. (1989)).

In a preferred embodiment of the invention, the deletion encompasses nucleic acid of the thyrotropin receptor gene encoding amino acid residues 317–366. In another embodiment of the invention, the deletion encompasses nucleic acid residues of the thyrotropin receptor cDNA encoding amino acid residues 317–366. In an embodiment of the invention, the deletion of either the thyrotropin receptor gene or cDNA, encompasses amino acid residues 315 to 364. In another embodiment the deletion encompasses amino acid residues 312 to 371. In yet another embodiment the deletion encompasses amino acid residues 307 to 376.

In another preferred embodiment, the replicatable vector is an expression vector. The term "expression vector" refers, in one embodiment, to a replicatable vector able to support the translation of part of its sequences into one or more peptides. The expression vector of this invention may replicate autonomously in the host cell, or may become integrated into the host cell DNA.

In yet another preferred embodiment, in term expression vector refers to a vector capable of supporting the transcription of part or all of its sequences into one or more transcripts. The vector according to this embodiment of the invention may replicate autonomously in the host cell, or may become integrated into the host cell DNA. Preparation of recombinant DNA molecules and expression vectors and their use to transform host cells is well known in the art (see e.g, Sambrook et al., *Molecular Cloning: A Laboratory Manual,* Cold Spring Harbor Laboratory, publisher, Cold Spring Harbor, N.Y. (1989)).

Any of a wide variety of vectors may be employed for this purpose Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmid such as those capable of replication in *E. coli* (such as, for example, pBR322, ColE1, pSC101, pACYC 184, πVX. Such plasmids are, for example, disclosed by Maniatis et al., (supra). Bacillus plasmids include pC194, pC221, pT127, etc. Such plasmids are disclosed by Gryczan (In: *The Molecular Biology of the Bacilli,* Academic Press, NY (1982) pp. 307–329) Suitable Streptomyces plasmids include pIJ101 (Kendall et al., *J. Bacteriol.* 169:4177–4183 (1987)) and steptomyces bacteriophages such as ΦC31 (Chater et al., In: *Sixth International Symposium on Actinomycetales Biology,* Akademiai Kaido, Budapest, Hungary (1986), pp. 45–54). Pseduomonas plasmids are reviewed by John et al., (Rev. Infect. Dis. 8:693–704 (1986)), and Izaki, (Jpn. J. Bacteriol. 33:729–742 (1978)).

Preferred eukaryotic plasmids include BPV, vaccinia, SV40, 2-micron circle, etc., or their derivatives. Such plamids are well known in the art (Bolstein et al., (Miami Wntr. Symp. 19:265–274 (1982); Broach, In: *The Molecular Biology of the Yeast Saccharomyces: Life Cycle and Inheritance,* Cold Spring Harbor Laboratory, Cold Spring Harbor, N.Y., p 455–470 (1981); Broach, Cell 28:203–204 (1982); Bollon, et al., *J. Clin. Hematol. Oncol.* 10:39–48 (1980); Sambrook, In: *Cell Biology: A Comprehensive Treatise, Vol.* 3, *Gene Expression,* Academic Press, N.Y. pp. 563–608 (1980)).

In yet another embodiment, the invention also provides a host cell comprising recominant DNA molecules according to the invention. According to this invention the term "host cell" refers to a cell which expresses the nucleotide sequences according to this invention.

Thus, according to this embodiment of the invention, once the vector or DNA sequence containing the construct(s) has been prepared for expression, the vector or DNA construct(s) may be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and micro-projectile (biolistic) bombardment (Johnston et al. Science 240(4858): 1538 (1988)).

After the introduction of the vector, recipient cells are grown in a selective medium, which selects for the growth of vector-containing cells. Expression of the cloned gene sequence(s) results in the production of the TSH receptor protein, or in the production of a fragment of this protein. This can take place in the transformed cells as such, or following the induction of these cells to differentiate.

The expressed protein may be isolated and purified in accordance with conventional conditions, such as extraction, precipitation, chromatography, affinity chromatography, electrophoresis, or the like. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, the TSH receptor or functional derivative thereof may be isolated by the use of anti-TSH receptor antibodies. Such antibodies may be obtained by well-known methods, some of which are mentioned hereinafter.

In a second aspect, the instant invention provides a recombinant thyrotropin receptor protein, or a functional or chemical derivative thereof, including a deletion capable of inhibiting cleavage at site 1. In an embodiment of the invention the deletion encompasses amino acids 317 to 366.

In a third aspect, the invention provides a recombinant nucleic acid sequence encoding for the thyrotropin receptor, or a functional or chemical derivative thereof, including a sequence encoding a cleavage-resistant moiety capable of resisting cleavage at cleavage site 2 in a replicatable vector. As used herein, the term "site 2" designates a site of proteolytic cleavage C-terminal to amino acid residue 317 in the thyrotropin receptor.

The term "cleavage-resistant moiety" is used herein to refer to one or more molecules linking amino acid residue 366 to 370 of the thyrotropin receptor protein providing a site for covalent modification of the recombinant protein, where such covalent modification prevents proteolytic cleavage at cleavage site 2. Covalent modifications according to this aspect of the invention, include but are not limited to, insertions of three or more amino acid residues or analogs thereof capable of preventing cleavage at site 2. According to this embodiment of the invention, the insertion of amino acids could, for example, fold into conformations preventing proteolytic cleavage of the receptor by steric hinderance. In an another embodiment of the invention, covalent modifications include the anchoring of prosthetic groups capable of preventing cleavage at site 2. Nonexclusive examples of such prosthetic groups include N-linked or O-linked glycosyl moieties, lipid moieties, peptide moieties, thiol containing moieties. In a preferred embodiment of this invention, the cleavage-resistant moiety is a consensus sequence for an N-linked glycosylation site.

In another embodiment of the invention, the replicatable vector is an expression vector. In yet another preferred embodiment, the term expression vector refers to a vector capable of supporting the transcription of part or all of its sequences into one or more transcripts. The vector according to this embodiment of the invention may replicate autonomously in the host cell, or may become integrated into the host cell DNA. Preparation of recombinant DNA molecules and expression vectors and their use to transform host cells is well known in the art (see e.g., *Molecular Cloning,* 2d Edition, Cold Spring Harbor Laboratory Press (1989)).

In yet another embodiment, the invention also provides a host cell comprising recombinant DNA molecules according to the invention.

In a fourth aspect, the instant invention provides a recombinant thyrotropin receptor protein, or a functional or chemical derivative thereof, including a sequence encoding a cleavage-resistant moiety capable of resisting cleavage at cleavage site 2 in a replicable vector. In a preferred embodiment according to this aspect of the invention, the cleavage-resistant moiety spans residues 367 to 369. In another embodiment, the cleavage-resistant moiety spans residues 365 to 371. In yet another embodiment, the cleavage-resistant moiety spans residues 360 to 376.

In an embodiment of the present invention, the recombinant nucleic acid sequence includes both a deletion capable of inhibiting cleavage at site 1, and a sequence encoding a cleavage-resistant moiety capable of resisting cleavage at cleavage site 2 in a replicatable vector. In a preferred embodiment of the invention, the recombinant nucleic acid sequence including both a deletion capable of inhibiting cleavage at site 1, and a sequence encoding a cleavage-resistant moiety capable of resisting cleavage at cleavage site 2 is an expression vector. In yet another embodiment of the invention, the recombinant nucleic acid sequence including both a deletion capable of inhibiting cleavage at site 1, and a sequence encoding a cleavage-resistant moiety capable of resisting cleavage at cleavage site 2 is in a host cell. In another embodiment, the invention also provides a recombinant thyrotropin receptor protein including both a deletion capable of inhibiting cleavage at site 1, and a sequence encoding a cleavage-resistant moiety capable of resisting cleavage at cleavage site 2. In a most preferred embodiment, the invention provides a recombinant thyrotropin receptor protein including both a deletion corresponding to amino acids 317 to 366, capable of inhibiting cleavage at site 1, and a cleavage-resistant moiety between amino acid residues 367 to 369 capable of resisting cleavage at cleavage site 2. In another most preferred embodiment, the invention provides a recombinant thyrotropin receptor protein including both a deletion corresponding to amino acids 317 to 366, capable of inhibiting cleavage at site 1, and a consensus sequence for an N-linked glycosylation site, capable of resisting cleavage at cleavage site 2.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector. The human thyrotropin receptor cDNA has been describe in co-pending U.S. application Ser. No. 07/722,620 filed Jun. 28, 1991, the specification of which is incorporated herein by reference as though set forth in full.

By "substantially pure" is meant any antigen of the present invention, or any gene encoding any such antigen, which is essentially free of other antigens or genes, respectively, or of other contaminants with which it might normally be found in nature, and as such exists in a form not found in nature. By "functional derivative" is meant the "fragments," "variants," "analogues," or "chemical derivatives" of a molecule. A "fragment" of a molecule, such as any of the cDNA sequences of the present invention, is meant to refer to any nucleotide subset of the molecule. A "variant" of such molecule is meant to refer to a naturally occurring molecule substantially similar to either the entire molecule, or a fragment thereof. An "analog" of a molecule is meant to refer to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences* 16th et., Mack Publishing Co., Easton, Pa. (1980).

Similarly, a "functional derivative" of a gene of the TSH receptor antigen of the present invention is meant to include "fragments," "variants," or "analogues" of the gene, which may be "substantially similar" in nucleotide sequence, and which encode a molecule possessing similar activity. Preferred functional derivatives include: recombinant active thyrotropin receptor wherein a 50 amino acid region comprising residues 317–366 has been deleted; a recombinant active thyrotropin receptor peptide comprised of the 8 amino acid region comprising residues 38–45; and a recombinant thyrotropin receptor peptide comprised of the mid-region domain C comprising amino acid residues 171–260.

Thus, as used herein, "thyrotropin receptor" or (TSH) protein is also meant to include any functional derivative, fragment, variant, analogue, or chemical derivative thereof.

A DNA sequence encoding the thyrotropin receptor of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook, T., et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequence involved with initiation or transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a thyrotropin receptor encoding sequence) are said to be operably linked if the nature of the linkage between the two DNA sequences does not (1) result in the introduction of a frame-shift mutation, (2) interfere with the ability of the promoter region sequence to direct the transcription of the thyrotropin receptor gene sequence, or (3) interfere with the ability of the thyrotropin receptor gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

In a fifth aspect, the invention provides a method of producing thyrotropin receptor by culturing a transformed cell according to the present invention under conditions allowing expression of thyrotropin receptor, and recovering said thyrotrophin receptor. Thus the present invention encompasses the expression of the thyrotropin receptor protein (or a functional derivative thereof) in either prokaryotic or eukaryotic cells, although eukaryotic (and, particularly, non-thyroidal eukaryotic) expression is preferred.

Preferred prokaryotic hosts include bacteria such as *E. coli*, Bacillus, Streptomyces, Pseudomonas, Salmonella, Serratia, etc. The most preferred prokaryotic host is *E. coli*. Other enterobacteria such as *Salmonella typhimurium* or *Serratia marcescens*, and various *pseudomonas* species may also be utilized. Under such conditions, the protein may not be glycosylated. The procaryotic host must be compatible with the replicon and control sequences in the expression plasmid.

To express the thyrotropin receptor protein (or a functional derivative thereof) in a prokaryotic cell (such as, for example, *E. coli, B. subtilis,* Pseudomonas, Streptomyces, etc.), it is necessary to functional prokaryotic promoter. Such promoters may be either constitutive or, more preferably, regulatable (i.e., inducible or depressible). Examples of constitutive promoters include the int promoter of bacteriophage X, the k1A promoter of the -lactamase gene of pBR322, and the CAT promoter of the chloramphenicol acetyl transferase gene of pBR325, etc. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., J. Bacteriol. 162:176–182 (1985)) and the α-28-specific promoters of *B. subtilis* (Gilman et al., *Gene* 32:11–20 (1984)), the promoters of the bacteriophages of Bacillus (Gryczan, In: *The Molecular Biology of the Bacilli*, Academic Press, Inc., NY (1982)), and Streptomyces promoters (Ward et al., Mol. Gen. Genet. 203:468–478 (1986)). Prokaryotic promoters are reviewed by Glick, (J. Ind. Microbiol. 1:277–282 (1987)); Cenatiempo, (Biochimie 68:505–516 (1986)); and Gottesman (Ann. Rev. Genet. 18:415–552 (1984)).

Proper expression in a prokaryotic cell also requires the presence of a ribosome binding site upstream of the gene-encoding sequence. Such ribosome binding sites are disclosed, for example, by Gold et al. (Ann. Rev. Microbiol. 35:365–404 (1981)).

Most preferred hosts are eukaryotic hosts including yeast, insects, fungi, and mammalian cells either in vivo, or in tissue culture. Mammalian cells provide post-translational modifications to protein molecules including correct folding or glycosylation at correct sites. Mammalian cells which may be useful as hosts include cells of fibroblast origin such as VERO or CHO-K1, or cells of lymphoid origin, such as the hybridoma SP2/O-AG1-4 or the myeloma P3x63Sg8, and their derivatives. CHO-K1 cells are presently preferred mammalian host cells. COS cells also are convenient eukaryotic hosts for thyrotropin receptor expression, as well as for study of the regulation of thyrotropin receptor expression.

For a mammalian cell host, many possible vector systems are available for the expression of TSH receptor. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

Yeast provides substantial advantages in that it can also carry out post-translational peptide modifications including glycosylation. A number of recombinant DNA strategies exist which utilize strong promoter sequences and high copy number of plasmids which can be utilized for production of the desired proteins in yeast. Yeast recognizes leader sequence on cloned mammalian gene products and secretes peptides bearing leader sequences (i.e., pre-peptides).

Further, by use of, for example, the yeast ubiquitin hydrolase system, in vivo synthesis of ubiquitin-TsH receptor fusion proteins may be accomplished. The fusion proteins so produced may be processed in vivo or purified and processed in vitro, allowing synthesis of the TSH receptor protein with a specified amino terminus sequence. Moreover, problems associated with retention of initiation codon-derived methionine residues in direct yeast (or bacterial) expression may be avoided. Sabin et al. Bio/Technol. 7(7): 705–709 (1989); Miller et al. Bio/Technol. 7(7): 698–704(1989).

Any of a series of yeast gene expression systems incorporating promoter and termination elements from the actively expressed genes coding for glycolytic enzymes produced in large quantities when yeast are grown in mediums rich in glucose can be utilized. Known glycolytic genes can also provide very efficient transcriptional control signals. For example, the promoter and terminator signals of the phosphoglycerate kinase gene can be utilized.

Production of TSH receptor or functional derivatives thereof in insects can be achieved, for example, by infecting the insect host with a baculovirus engineered to express TSH receptor by methods known to those of skill. Thus, in one embodiment, sequences encoding human TSH receptor may be operably linked to the regulatory regions of the viral polyhedron protein (Jasny, Science 238: 1653 (1987)). Infected with the recombinant baculovirus, cultured insect cells, or the live insects themselves, can produce the TSH receptor protein in amounts as great as 50% of total protein production. When live insects are to be used, caterpillar are presently preferred hosts for large scale TSH receptor production according to the invention.

As discussed above, expression of the throtropin receptor protein in eukaryotic hosts requires the use of eukaryotic regulatory regions. Since regions will, in general, include a promoter region sufficient to direct the initiation of PHA synthesis. Preferred eukaryotic promoters include the promoter of the mouse metallothionein I gene (Hamer et al., J. Mol. Appl. Gen. 1:273–288 (1982)); the TK promoter of Herpes virus (McKnight, Cell 31:355–365 (1982)); the SV40 early promoter (Benoise et al., Nature (London) 290:3O4–310 (1981)); the yeast gal4 gene promoter (Johnston et al., Proc. Natl. Acad. Sci.(USA) 79:6971–6975 (1982); Silver et al., Proc. Natl. Acad. Sci. (USA) 81:5951–5955 (1984)). Of these, presently the most preferred is the SV40 promoter.

As is widely known, translation of eukaryotic mRNA is initiated at the codon which encodes the first methionine. For this reason, it is preferable to ensure that the linkage between a eukaryotic promoter and a DNA sequence which encodes the TSH receptor protein (or a functional derivative thereof) does not contain any intervening codons which are capable of encoding a methionine (i.e., AUG). The presence of such codons results either in a formation of a fusion protein (if the AUG codon is in the same reading frame as TSH receptor encoding DNA sequence) or a frame-shift mutation (if the AUG codon is not in the same reading frame at the TSH receptor encoding Sequence).

The TSH receptor encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the the' TSH receptor protein may occur through the transient expression of the introduced sequence. Alternatively, permanent exposure may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allows for selection of host cells which contain the expression vector. The marker may provide for prototrophy to an auxotropic host, biocid resistance, e.g., antibiotics, or heavy metals, such as copper or the like. The selectable marker gene can be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, Mol. Cel. Biol. 3:280 (1983).

In a sixth aspect, the present invention comprises antibodies against the TSH receptor protein, or a functional derivative thereof. The term "antibody" (Ab) or "monoclonal antibody" (Mab) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation and may have less non-specific tissue binding of an intact antibody (Wahl et al., J. Nucl. Med. 24:316–325 (1983)).

Antibodies according to the present invention may be prepared by any of a variety of methods. For example, cells expressing the TSH receptor protein, or a functional derivative thereof, can be administered to an animal in order to induce the production of sera containing polyclonal antibodies that are capable of -binding TSH receptor.

In a preferred method, antibodies according to the present invention are monoclonal antibodies. Such monoclonal antibodies can be prepared using hybridoma technology (Kohler et al., Nature 256:495 (1975); Kohler et al., Eur. J. Immunol. 6:511 (1976); Hammerling et al. In: *Monoclonal Antibodies and T-Cell* Elsevier, N.Y., pp. 563–681 (1981). In general, such procedures involve immunizing an animal with TSH receptor antigen. The splenocytes of such animals are extracted and fused with a suitable myeloma cell line. Any suitable myeloma cell line may be employed in accordance with the present invention. After fusion, the resulting hybridoma cells are selectively maintained in HAT meduim, and then cloned by limiting dilution as described by Wands et al., Gastro-enterology 80:225–232 (1981). The hybridoma cells obtained through such a selection are then assayed to identify clones which secrete antibodies capable of binding the TSH receptor antigen.

Antibodies according to the present invention also may be polyclonal, or, preferably, region specific polyclonal antibodies. Region specific polyclonal antibodies and methods of using them are described in co-pending U.S. application Ser. No. 06/731,470, filed May 07, 1985, the specification of which is incorporated herein by reference as though set forth in full.

Antibodies against TSH receptor a functional derivative thereof, according to the present invention are well suited for use in standard immunodiagnostic assays known in the art, including such immunometric or "sandwich" assays as the forward sandwich, reverse sandwich, and simultaneous sandwich assays. The antibodies may be used in any number of combinations as may be determined by those of skill without undue experimentation to effect immunoassays of acceptable specificity, sensitivity, and accuracy for the TSH receptor antigen or equivalents thereof.

Standard reference works setting forth general principles of immunology include Roitt, I., *Essential Immunology*, Sixth Ed., Blackwell Scientific Publications, Publisher, Oxford (1988); Kimball, *Indroduction to Immunology*, Second Ed., Macmillan Publishing Co., Publisher, New York (1986); Roitt et al., *Immunology*, Gower Medical Publishing Ltd., Publisher, London, (1985); Campbell, "Monoclonal Antibody Technology," in, Burdon, R, et al., eds., *Laboratory Techniques in Biochemistry and Molecular Biology*, Volume 13, Elsevier, Publisher, Amsterdam (1984); Klein, *Immunology: The Science of Self-Nonself Discrimination*, John Wiley & Sons, Publisher, New York (1982); and Kennet et al., eds., *Monoclonal Antibodies Hybridoma: A New Dimension in Biological Analyses*, Plenum Press, Publisher, New York (1980).

By "detecting" it is intended to include determining the presence or absence of a substance or quantifying the amount of a substance. The term thus refers to the use of the materials, compositions, and methods of the present invention for qualitative and quantitative determinations.

The isolation of other hybridomas secreting monoclonal antibodies of the same specificity as those descirbed herein can be accomplished by the technique of anti-idiotypic screening. Potocmjak et al., Science 215:1637 (1982). Briefly, and anti-idiotypic antibody is an antibody which recognizes unique determinants present on the antibody produced by the clone of interest. The anti-idiotypic antibody is prepared by immunizing an animal of the same strain used as the source of the monoclonal antibody with the monoclonal antibody of interest. The immunized animal will recognize and respond to the idiotypic determinants of the immunizing antibody by producing antibody to these idiotypic determinants (anti-idiotypic antibody).

By using the anti-idiotypic antibody of the second animal, which is specific for the monoclonal antibodies produced by a single clone, it is then possible to identify other clones used for immunization. Idiotypic identity between the product of two clones demonstrates that the two clones are identical with respect the their recognition of the same determinants. The anti-idiotypic antibody may also be used as an "immunogen" to induce an immune response in yet another animal, producing a so-called anti antiidiotypic antibody which will be epitopically identical to the original MAb. Thus, by using anti-bodies to the epitopic determinants of a monoclonal antibody, it is possible to identify other clones expressing antibodies of identical epitopic specificity. In antibodies, idiotypic determinants are present in the hypervariable region which binds to a given epitope.

Accordingly, monoclonal antibodies generated against the TSH receptor antigen or functional derivative thereof may be used to induce antiidiotypic Abs in suitable animals, such as BALB/c mice. Spleen cells from these animals are used to produce anti-idiotypic hybridoma cell lines. Monoclonal anti-idiotypic Abs coupled to KLH are used as "immunogen" to immunize BALB/c mice. Sera from these mice will contain anti and anti-idiotypic Abs that have the binding properties of the original Ab specific for the shared epitope. The anti-idiotypic MAbs thus have idiotopes structurally similar to the epitope being evaluated.

For replication, the hybrid cells may be cultivated both in vitro and in vivo. High in vivo production makes this the presently preferred method of culture. Briefly, cells from the individual hybrid strains are injected intraperitoneally into pristane-primed BALB/c mice to produce ascites fluid containing high concentrations of the desired monoclonal antibodies. Monoclonal antibodies of isotype IgM or IgG may be purified from cultured supernatants using column chromatography methods well known to those of skill in the art.

Antibodies according to the present invention are particularly suited for use in immunoassays wherein they may be utilized in liquid phase or bound to a solid phase carrier. In addition, the antibodies in these immunoassays can be detectably labeled in various ways.

There are many different labels and methods of labeling known in the art. Examples of the types of labels which can be used in the present invention include, but are not limited to, enzymes, radioisotopes, fluorescent compounds, chemiluminescent compounds, bioluminescent compounds and metal chelates. Those of ordinary skill in the art will know of other suitable labels for binding to antibodies, or will be able to ascertain the same by the use of routine experimentation. Furthermore, the binding of these labels to antibodies can be accomplished using standard techinques commonly known to those of ordinary skill in the art.

One of the ways in which antibodies according to the present invention can be detectably labeled is by linking the antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label antibodies includes malate dehydrogenase, staphylococcal nuclease, delta-V-steriod isomerase, yeast alcohol dehydrogenase, alpha-glycerophosphate dehydrogenase, triose phosphate isomerase, biotin-avidin peroxidase, horseradish peroxidase, alkaline phosphatase, asparaginase, glucose oxidase, betagalactosidase, ribonuclease, urease, catalase, glucose-VI-phosphate dehydrogenase, glucoamylase and acetylcholine esterase.

The presence of detectably labeled antibodies also can be detected by labeling the antibodies with a radioactive isotype which then can be determined by such means as the use of a gamma counter or scintillation counter. Isotopes which are particularly useful for the purpose of the present invention are $^3H$, $^{125}I$, $^{32}P$, $^{35}P$, $^{14}C$, $^{51}Cr$, $^{36}Cl$, $^{57}Co$, $^{58}Co$, $^{59}Fe$ and $^{75}Se$.

It is also possible to detect the binding of detectalby labeled antibodies by labeling the antibodies with a fluorescent compound. When a fluorescently labeled antobody is exposed to light of the proper wave length, its presence then can be detected due to the fluorescence of the dye. Among the most commonly used fluorescent labeling compounds are fluoroscein, isothiocyanate, rhodamine, phycoerythrin, phycocyanin, allophycocyanin, o-phthal-dehyde and fluorescamine.

The antibodies of the invention also can be detectably labeled using fluorescent emitting metals such as $^{152}Eu$, or others of the anthanide series. These metals can be attached to the antibody molecule using such metal chelating groups as diethyl enetriaminepentaacetic acid (DTPA) or ethylene-diaminetetraacetic acid (EDTA).

Antibodies also can be detectably labeled by coupling them to a chemiluminescent compound. The presence of the chemiluminescent-tagged antibody is then determined by detecting the presence of luminescence that arises during the course of the chemical reaction. Examples of particularly useful chemiluminescent labeling compounds are luminal, isoluminol, theromatic acridinium ester, imidazole, acridinium salts, oxalate ester, and dioxetane.

Likewise, a bioluminescent compound may be used to label the antibodies according to the present invention. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labeling include luciferase and aequorin.

The antibodies and substantially purified antigen of the present invention are ideally suited for the preparation of a kit. Such a kit may comprise a carrier means being compartmentalized to receive in close confinement therewith one or more container means such as vials, tubes and the like, each of said container means comprising the separate elements of the assay to be used.

The types of assays which can be incorporated in kit form are many, and include, for example, competitive and non-competitive assays. Typical examples of assays which can utilize the antibodies of the invention are radioimmunoassays (RIA), enzyme immunoassays (EIA), enzyme-linked immunosorbent assays (ELISA), and immunometric, or sandwich, immunoassays.

By the term "immunometric assay" or "sandwich immunoassay," it is meant to include simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Forward sandwich assays are described, for example, in U.S. Pat. Nos. 3,867,517; 4,012,294 and 4,376,110. Reverse sandwich assays have been described, for example, in U.S. Pat. Nos. 4,098,876 and 4,376,110.

In the preferred mode for preforming the assays it is important that certain "blockers" be present in the incubation medium (usually added with the labeled soluble antibody). The "blockers" are added to assure that non-specific proteins, protease, or human antibodies to mouse immunoglobulins present in the experimental sample do not cross-link or destroy the antibodies on the solid phase support, or the radiolabeled indicator antibody, to yield false positive or false negative results. The selection of "blockers" therefore adds substantially to the specificity of the assays described in the present invention.

It has been found that a number of (i.e. nonspecific) antibodies of the same class or subclass (isotype) as those used in the assays (e.g. $IgG_1$, $IgG_{2a}$, IgM, etc.) can be used as "blockers." The concentration of the "blockers" (normally 1–100 microgs/microl) is important in order to maintain the proper sensitivity yet inhibit any unwanted interference by mutually occurring cross reactive proteins in human serum. In addition, the buffer system containing the "blockers" needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01–10 microgs/ml) to the buffer which contains the "blockers."

There are many solid phase immunoadsorbents which have been employed and which can be used in the present invention. Well known immunoadsorbents include glass, polystyrene, polyproplenes dextran, nylon and other materials, in the form of tubes, beads, and microtiter plates formed from or coated with such materials, and the like. The immobilized antibodies can be either covalently or physically bound to the solid phase immunoadsorbent, by techniques such as covalent bonding via an amide or ester linkage, or by adsorption. Those skilled in the art will known many other suitable solid phase immunoadsorbents and methods for immobilizing antibodies thereon, or will be able to ascertain such, using no more than routine experimentation.

In a particular embodiment, the invention provides a pure antigen TSH receptor, or a functional derivative thereof, which may be used to detect or measure antibody to TSH receptor in a sample, such as serum or urine, using an automated diagnostic system. In a particularly preferred embodiment, the automated diagnostic system is a microsystem platform suitable to manipulate the sample For in vivo, in vitro or in situ diagnosis, labels such as radiolabels may be bound to antibodies according to the present invention either directly or by using an intermediary functional group. An intermediary group which is often used to bind radioisotopes which exist as metallic cations to anti-bodies is diethylenetriaminepentaacetic acid (DTPA). Typical examples of metallic cations which are bound in this manner are: $^{99m}Tc$, $^{123}I$, $^{111}IN$, $^{131}I$, $^{97}Ru$, $^{67}Cu$, $^{67}Ga$ and $^{68}Ga$. The antibodies of the invention can also be labeled with non-radioactive isotopes for purposes of diagnosis. Elements which are particularly useful in this manner are $^{157}Gd$, $^{55}Mn$, $^{162}Dy$, $^{52}Cr$ and $^{56}Fe$.

The DNA sequences which encode TSH receptor, or a fragment thereof, may be used as DNA probes to isolate the corresponding antigen in humans according to well-known methods. The human antigen genes may then be cloned and expressed in a host to give the human antigen. This human antigen may then be used in diagnostic assays for the corresponding auto-antibody.

The antigen of the invention may be isolated in substantially pure form employing antibodies according to the present invention. Thus, an embodiment of the present invention provides for substantially pure antigen TSH receptor or functional derivative thereof, said antigen characterized in that it is recognized by, and binds to antibodies according to the present invention. In another embodiment, the present invention provides a method of isolating or purifying the TSH receptor antigen, by forming a complex of said antigen with one or more antibodies directed against TSH receptor or functional derivative thereof.

The substantially pure antigen TSH receptor or functional derivative of the present invention may in turn be used to detect or measure antibody to TSH receptor in a sample, such as serum or urine. Thus, one embodiment of the present invention comprises a method of detecting the presence or amount of antibody to TSH receptor antigen in a sample, comprising contacting the sample containng an antibody to TSH receptor antigen with the detectably labeled TSH receptor, to detect the label. It will be appreciated that immunoreactive fractions and immunoreactive analogues of TSH receptor also may be used. By the term "immunoreactive fraction" is intended any portion of the TSH receptor antigen which demonstrates an equivalent immune response to an antibody directed against TSH receptor. By the term "immunoreactive analogue" is intended a protein which differs from the TSH receptor protein by one or more amino acids, but whch demonstrates an equivlent immunoresponse to an antibody of the invention.

The pharmaceutical compositions of the invention may be administered to any animal which may experience the beneficial effects of the compounds of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

In addition to the pharmacologically active compounds the new pharmaceutical preparations may contain suitable pharmaceutically acceptable carriers comprising excipients and auxiliaries which facilitate processing of the active compounds into preparations which can be used pharmaceutically preferably, the preparations, particularly those preparation which can be administered orally and which can be used for the preferred type of administration, such as tablets dragees and capsules and and also preparations which can be administered rectally, such as suppositories as well as suitable solutions for administration by injection or orally, contain from about 0.01 to 99 percent, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients optionally grinding the resulting mixtures and processing the mixture of granules, after adding suitable auxiliaries, if desired or necessary, to obtain tablets or dragee cores.

Suitable excipients are, in particular, fillers such as saccharides for example lactose or sucrose, mannitol or sorbitol, cellulose preparations and/or calcium phosphates for example tricalcium phosphate or calcium hydrogen phosphate, as well as binders such as Starch paste, using, for example, maize starch, wheat starct, rice starch, potato starch, gelatin, tragacanth, methyl cellulose, hydroxy pylmethylcellulose, sodium carboxymethylcellulose, and/or polyvinyl pyrrolidone. If desired, disintegrating agents may be added such as, for example, the above-mentioned starches and also carboxymethyl-starch cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcuim stearate, and/or polyehtylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable Organic solvents or solvent mixtures. In order to produce coatings resistant to gastric juices, solutions of suitable cellulose preparations such as acetyl-cellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liqiud triglycerides, polyethylene glycols, or paraffin hydrocarbons.

Suitable formulation for parenteral administration include aqueous solutions of the active compounds in water-soluble form, for example, water-soluble salts. In addition, suspensions of the active compounds as appropriate oily injection suspensions may be administered. Suitable lipophilic solvents or vehicels include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The substantially pure antigen TSH receptor of the present invention may be used in pharmacologically effective amounts in pharmaceutical preparations to treat thyrotoxicosis. In Graves' disease, the most common form of thyrotoxicosis, anti-TSH receptor autoantibodies bind to TSH receptor on the thyroid cell surface. Such binding causes unregulated stimulation of the thyroid cell which then produces excessive amounts of thyroid hormone. Tolerance to anti-TSH receptor auto-antibodies may be induced in patients by the injection of pharmaceutically effective amounts of recombinant TSH receptor, or a functional or chemical derivative thereof. As more recombinant TSH receptor is introduced, a higher percentage of the auto-antibodies present combine with the recombinant TSH receptor as opposed to the naturally occurring TSH receptor on the thyroid cell surface. As less auto-antibodies combine with the cell bound TSH receptor, the thyroid cells are less stipulated and thyroid hormone production becomes subject to the regulation of thyrotropin.

Auto immune disease are thought to occur when thymus-derived lymphocytes (T cell) become persistently activated by self antigens (Janeway, Nature 341:482 (1989)). In the case of autoimmune thyrotoxicosis, this self antigen is the epitope of the TSH receptor which is recognized by a receptor on the autoimmune T cells. The present invention allows the determination of this epitope of the TSH receptor using standard techniques commonly known to those of ordinary skill in the art. Further, the present invention makes possible the characterization of the auto immune T-cell receptor (TCR) specific to the TSH receptor using methods described in, for example, Burns et al., J. Exp. Med. 169:27 (1989). If the autoimmune T cells can be eliminated or prevented from reacting with the TSH receptor, the effects of thyrotoxicosis may be greatly alleviated. T cells that will accomplish this objective may be generate which are specific for the autoimmune TCR for TSH receptor using methods described in, for example, Acha-Orbea et al., Ann. Rev. Immunol. 7:371 (1989).

Thus in one embodiment of the invention, a T cell is provided which is specific for auto immune TCR for TSH receptor. Another embodiment of the invention provides for a pharmaceutical preparation comprising a T cell which is specific for the auto immune TCR for TSH receptor. In yet another embodiment of the current invention, a method of treating autoimmune thyrotoxicosis is provided comprising the use of a pharmaceutical preparation comprising a T cell which is specific for the autoimmune TCR for TSH receptor.

Upon characterization of the auto immune TCR for TSH receptor, peptides may be generated to interfere with the autoimmune TCR using methods described in, for example, Vandenbark et al,. Nature 341:541 (1989) and Janeway, Nature 341:482 (1989). Such interference would reduce the interaction between the autoimmune T cells and the TSH receptor, greatly reducing the effects of autoimmune thyrotoxicosis.

Thus in anther embodiment of the invention, a peptide is provided which is specific for the auto immune TCR for TSH receptor. Another embodiment of the invention provides for a pharmaceutical preparation comprising a peptide which a specific for the autoimmune TCR for TSH receptor. In yet another embodiment of the current invention, a method of treating auto immune thyrotoxicosis is provided comprising the use of a pharmaceutical preparation comprising a peptide which is specific for the auto-immune TCR for TSH. receptor.

A class of T cells, known as suppressor T cells, mediate the immunity suppressor system. These cells provide a mechanism for turning off immune responses that otherwse might overwhelm the host.

When an animal is exposed to an excess of antigen to which it is genetically nonresponsive, several events take place. Benacerraf, In: *The Biology of Immunologic Disease*, HP Publishing Co., Inc., NY, pp. 49–62 (1983). Antigen first induces a population of suppressor T cells. These lymphocytes elaborate a soluble factor that combines with small quantities of antigen and induces a second suppressor T-cell clone. It is these effector cells that actually suppress the antibody-producing B cells. It is likely that this system serves the homeostatic role of turning off antibody response that threatnes to overwhelm the host. To treat thyrotoxicosis, animals are exposed to excess amounts of thyrotropin receptor and the resulting suppressor T cells specific for antithyrotropin receptor auto-antibodies are harvested using methods as described in, for example, Green, D., et al., Ann. Rev. Immunol. 1:439 (1983) or Benacerraf, In: *The Biology of Immunologic Disease*, HP Publishing Co., Inc., NY, pp. 49–62 (1983). Patients with thyrotoxicosis are treated with the suppressor T cells so as to suppress the formation of antithyrotropin receptor auto-antibodies. The suppression of the auto-antibody production would greatly lessen or eliminate the effects of thyrotoxicosis.

Thus in one embodiment of the invention, a suppressor T cell is provided which is specific for anti-thyrotropin receptor auto-antibodies. Another embodiment of the invention provides for a pharmaceutical preparation comprising a suppressor T cell which is specific for anti-thyrotropin receptor auto-antibodies. In yet another embodiment of the current invention, a method of treating autoimmune thyrotoxicosis is provided comprising the use of a pharmaceutical preparation comprising a suppressor T cell which is specific for anti-thyrotropin receptor auto-antibodies. In yet another embodiment of the current invention, a method of treating autoimmune thyrotoxicosis is provided comprising the use of a pharmaceutical preparation comprising a suppressor T cell which is specific for anti-thyrotropin receptor auto-antibodies.

The manner and method of carrying out the present invention may be more fully understood by those of skill by reference to the following examples, which examples are not intended in any manner to limit the scope of the present invention or of the claims directed thereto.

EXAMPLE 1

Effect of Trypsin on Cell Surface TSHR Subunit Structure

In TSHR-10,000, a Chinese hamster ovary (CHO) cell line, overexpression of the human TSHR ($\sim 2 \times 10^6$ receptors per cell) was attained by transgenome amplification using a dihydrofolate reductase minigene (e.g., Chazenbalk et al., Endocrinology 137:4586–4591 (1986)). These cells, as well as CHO cells expressing TSHR mutants (unamplified transgenomes), were propagated in Ham's F-12 medium supplemented with 10% fetal calf serum (FCS), penicillin (100 U/ml), gentamicin (50 $\mu$g/ml) and amphotericin B (2.5 $\mu$g/ml). The availability of CHO cells overexpressing the TSHR ($\sim 2$ million receptors per cell) made it feasible to study the effect of trypsin on the structure of the mature TSHR expressed on the surface of precursor-labeled intact cells.

TSHR-10,000 cell proteins precursor labeled (1 hour) followed by an overnight chase and subsequent exposure to trypsin. Cells remained in monolayer culture throughout the procedure. After detergent extraction of the cells, TSHR were immunoprecipitated with a mouse mAb to the extreme N terminus of the TSHR A subunit. Precipitates were subjected to SDS-polyacrylamide gel (10%) electrophoresis under reducing conditions followed by autoradiography. Identification of the indicated bands has been reported previously (5). Complex and high mannose refer to the type of glycan, determined by differential sensitivity to endoglycosidase H and F. The apparently paradoxical detection of the B subunit with a mAb to the A subunit is explained by the disulfide linkage of these two subunits, subsequently separated by reduction. The lesser amount of B than A subunit is typical in such experiments and is probably secondary to loss of B subunit tethered to the A subunit during the stringent washing procedure.

Figure 1:
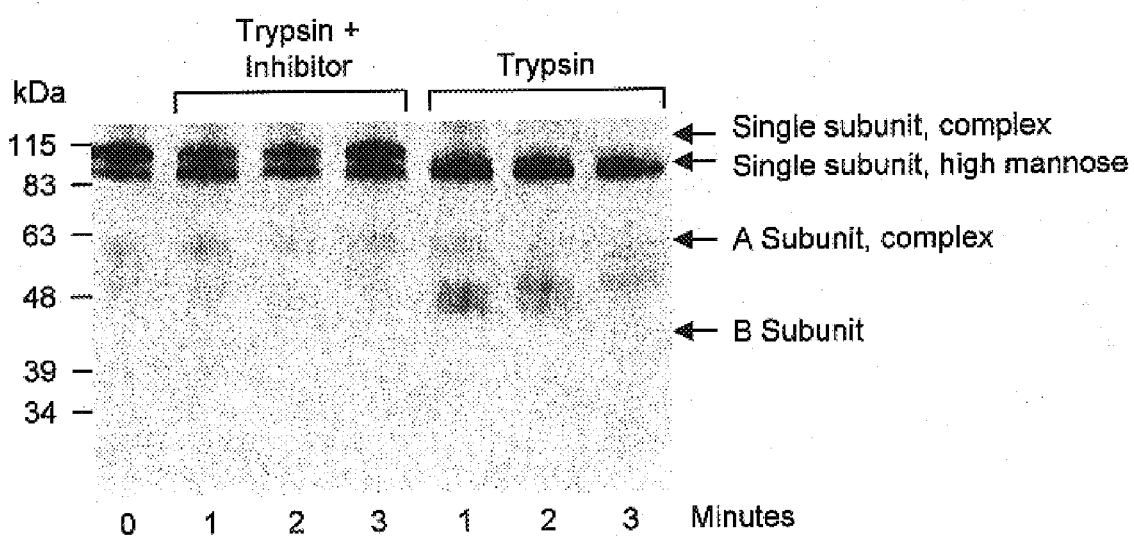
FIG. 1: is a representation of a Wester blot showing the effect of trypsin on intact CHO cells expressing the human TSH receptor.

As shown in FIG. 1, light trypsinization of cells in monolayer prior to solubilization for immunoprecipitation completely abolished the single chain TSHR with mature, complex carbohydrate and had no effect on the single chain receptor with immature, high mannose carbohydrate. These data are consistent with an effect of trypsin only at the cell surface and support the concept that TSHR with complex, but not high mannose, glycan traffick to the cell surface.

As shown therein, trypsinization also had a marked effect on the subunits of the cleaved receptors. The mature A subunit with complex carbohydrate ($\sim 60$ kDa), became less intense and more diffuse. Detection of the B subunit was virtually abolished. Most important from the point of view of TSHR subunit structure, was the marked intensification of bands migrating at $\sim 50$ kDa concurrent with the loss of single chain receptor. Because they are larger than the B subunit and because they are detected with a mAb to the extreme A terminus of the A subunit (epitope at residues 22–35, with the signal peptide being residues 1–21), these bands must be smaller than normal A subunits, truncated at their carboxyl-termini. The strong intensity of the these "small" A subunits establishes that they arise predominantly from the effect of trypsin on the single chain, mature TSHR on the cell surface (the only stronger band prior to trypsinization). A smaller component may arise from the A subunits of of normal size. The appearance of the $\sim 50$ kDa bands as a doublet has not been elucidated but may represent incomplete cleavage at Site 2 (see also FIG. 2).

TSHR-10,000 cells in monolayer were treated for 2 min with trypsin in the presence or absence of trypsin inhibitor prior to preparation of 100–10,000×g particulate fractions. Where indicated, aliquots were treated with endoglycosidase H or F (Methods). The crude membrane preparations were then subjected to SDS-PAGE (10%) under reducing conditions, electroblotted onto membranes and probed with a mouse mAb (A10) to the A subunit (amino acids 22–35).

TSHR-10,000 cells in monolayer were treated for 2 min with trypsin in the presence or absence of trypsin inhibitor prior to $^{125}$I-TSH binding and crosslinking.

Figure 3A:
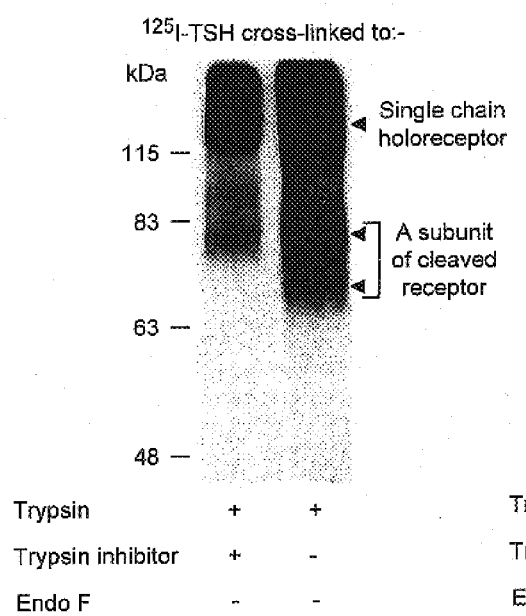
FIG. 3: is a representation of a Western blot showing TSH crosslinking to TSHR on the surface of intact cells confirming that the TSHR fragment released by trypsin contains glycan.
Figure 3B:
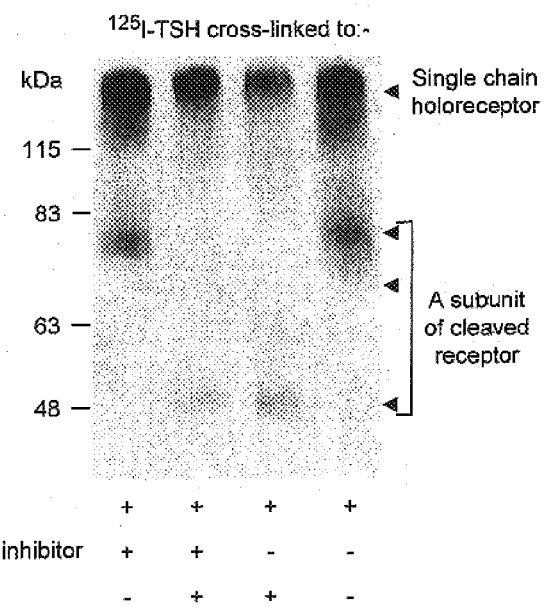

The 100–10,000×g particulate fractions from these cells were subjected to SDS-PAGE (10%) under reducing conditions. Where indicated, aliquots of the crude membrane preparations were treated with endoglycosidase F (Methods). Notes the greater separation of the TSH-linked glycosylated A subunit doublet in panel A with more prolonged electrophoresis. In panel B, electrophoresis was shorter in order to visualize the deglycosylated TSH-A subunit adducts (see FIG. 3).

Figure 2:
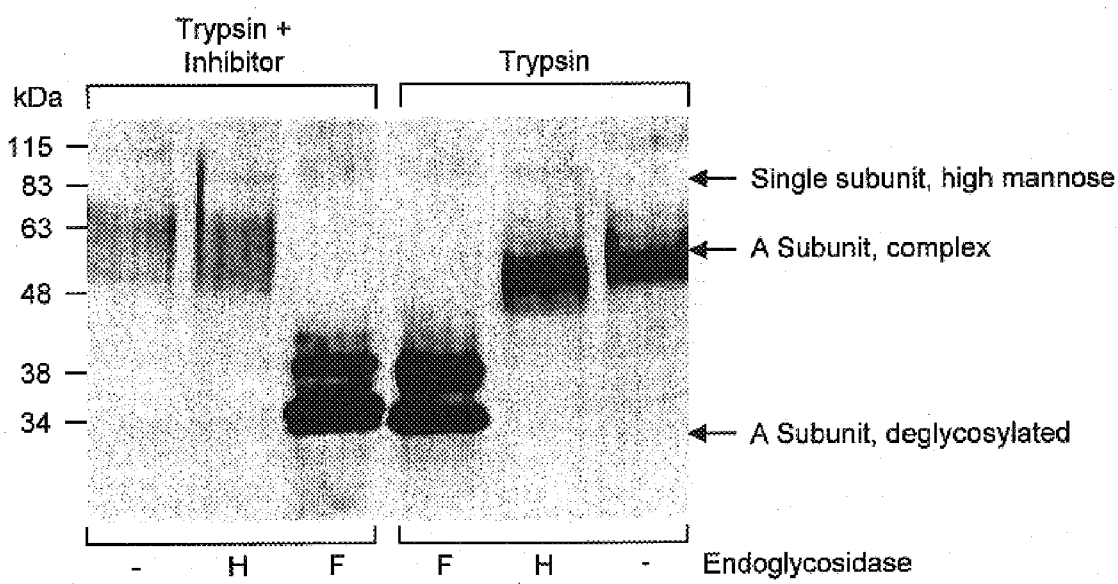
FIG. 2: is a representation of a Western blot showing the trypsin-induced reduction in A subunit size is greater for the glycosylated than for the deglycosylated A subunit.

Immunoblotting as shown in FIG. 2 provides a "steady state" glimpse of the TSHR and its subunits in particulate fractions from the same TSHR-10,000 cells. Under these conditions, the cleaved receptor is the dominant structure, as detected by the mature A subunit with complex carbohydrate (endoglycosidase H resistant). Only a small amount of single chain receptor with high mannose glycan is evident. Also in contrast to the immunoprecipitations, the B subunit is not detected because it is released by reduction before immunodetection. Antibodies to the B subunit obtained have not provided the sensitivity or specificity of the A sbunit mAb. Consistent with the immunoprecipitation experiments, light trypsinization of intact cells prior to homogenization reduced most of the very broad ~50–60 kDa A subunit band to a focused band at ~50 kDa.

FIG. 2 also shows that the trypsin-induced reduction in A subunit size was much greater for the glycosylated A subunit (up to 10 kDa) than for the enzymatically deglycosylated A subunit (1–2 kDa) suggesting that the fragment of the A subunit polypeptide chain removed by trypsin contains a glycosylation site. Moreover, because the epitope of mAb used for detection is at the extreme amino terminus of the A subunit, the trypsin fragment is likely to be released from the C terminus of the A subunit. This observation in numerous experiments suggests a "large" A subunit cleaved only a Site 2, rather than incomplete diglycosylation.

Figure 4:
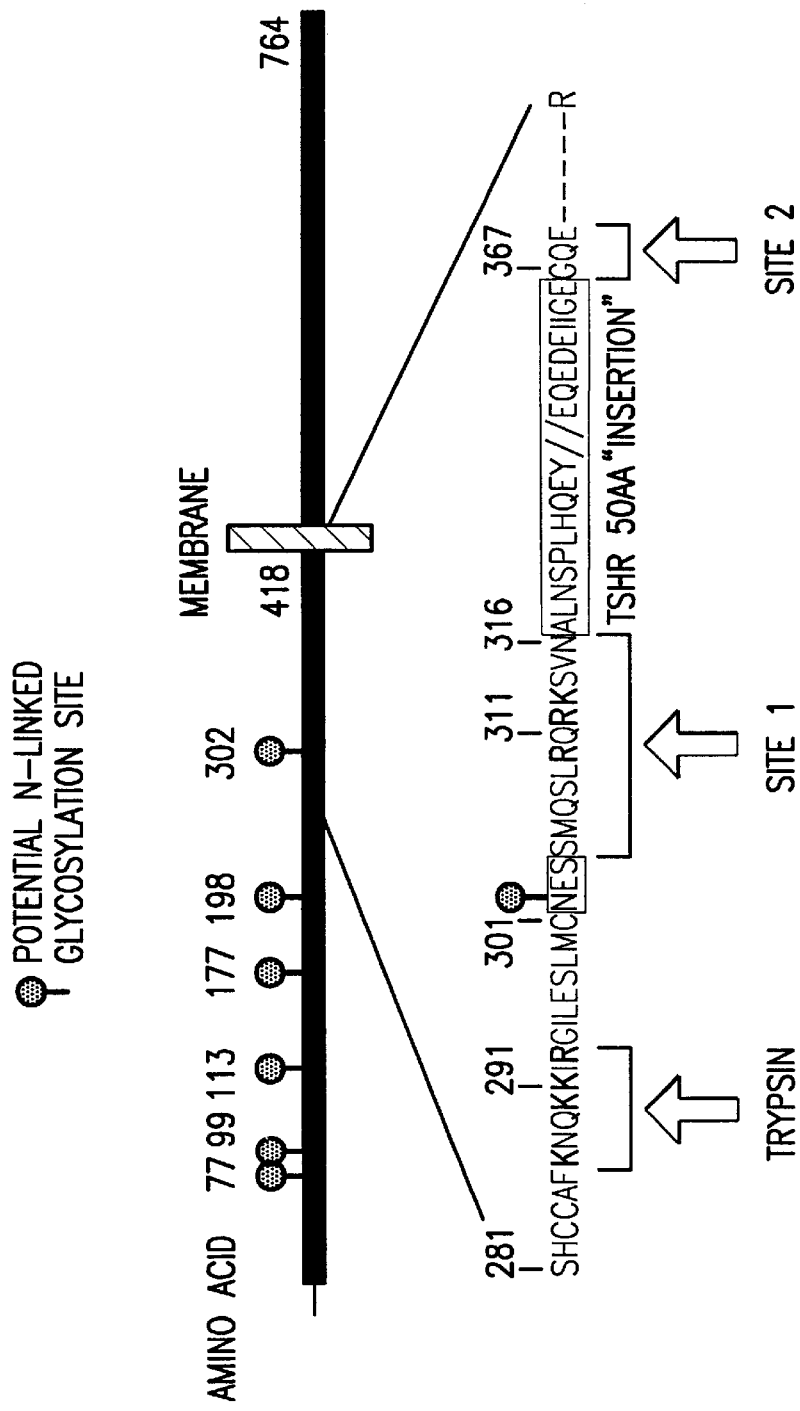
FIG. 4: is a schematic representation of the TSHR, with emphasis on the regions of spontaneous and trypsin-induced cleavage. Site 1 indicates the region involved at the TSHR upstream cleavage site, as deduced from the present study. The horizontal shaded bar is included as a quantitative reference to indicate the maximum size (2 kDa) of the polypeptide fragment released by trypsin from the C terminus of the A subunit (see FIG. 2). Cleavage by trypsin upstream of the glycan at residue 302 must occur at the indicated cluster of R and K residues. The next potential cleavage site upstream trypsin site (R273) would yield a tryptic fragment (encompassing N302) of 3 kDa, far greater than observed experimentally. Site 2 refers to the amino acid triplet that, when substituted with the corresponding N-linked glycosylation motif at the homologous region of the LH/CGR ($GQE_{367-369}NET$), abrogates cleavage.

Confirmation of the presence of a glycan moiety on the tryptic fragment released by trypsin from the A subunit was obtained by $^{125}$I-TSH crosslinking studies to the TSHR on the surface of the intact TSHR-10,000 cells. Thus, after light trypsiniation, TSH crosslinked to TSHR with both a normal sized A subunit (~74 kDa adduct including a TSH subunit) and a "small" A subunit (~67 kDa adduct) (see FIG. 3A). Again, after enzymatic deglycosylation of these TSH-TSHR complexes, this large (5–10 kDa) difference in A subunit size was reduced to 1–2 kDa (see FIG. 3B). Examination of the potential N-linked glycosylation sites on the human TSHR establishes N302, the sixth and last such site, as the only possible contributor to the N-linked glycan moiety removed by trypsin from the C terminus of the TSHR A subunit (see FIG. 4). Thus, clipping by trypsin of the next, upstream glycan would be at amino acid residue 198 (numbering includes a 21 residue signal peptide) and would produce a polypeptide backbone of only 20 kDa, far samller than that observed experimentally (see FIG. 2).

The presence of both normal and small A subunits after trypsinization (see FIG. 3A) was consistently observed in these cross-linking experiments and contrasted with the far lower presence of normal size A subunits on immunoblotting (see FIG.2). Most likely this phenomenon is attributable to the fact that the 2 hour TSH binding period prior to covalent crosslinking permits trafficking to the cell surface of intracellular TSHR left unscathed by the effect of trypsin only on the cell surface.

EXAMPLE 2

THSR A Subunit Size

Figure 5:
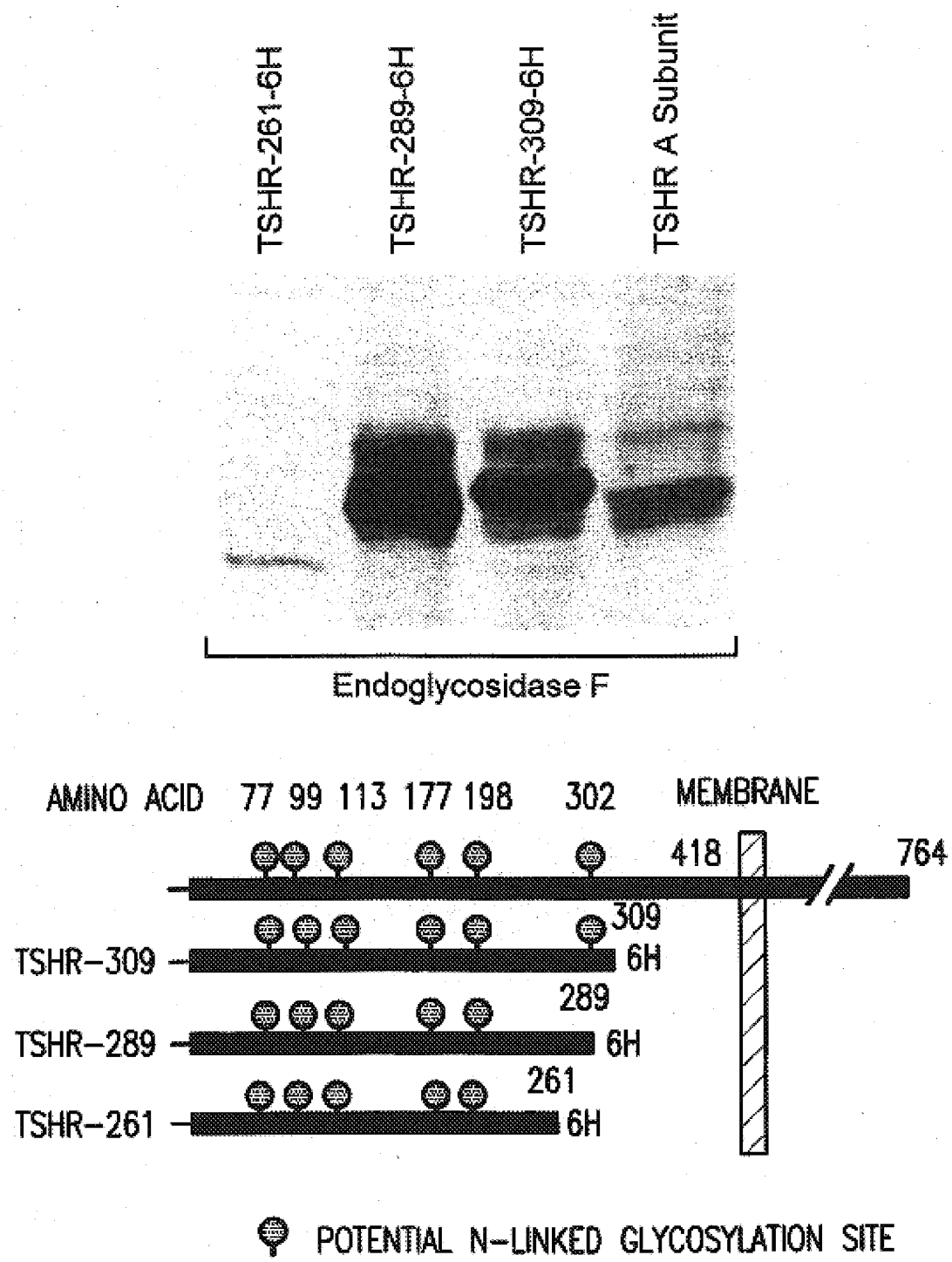
FIG. 5: is a representation of a Western blot showing the polypeptide backbone of the deglycosylated TSHR A subunit, cleaved spontaneously at Site 1, is smaller than that of deglycosylated ectodomain variant TSHR-309-6H.

The size of the A subunit polypeptide chain, estimated to be ~35 kDa relative to standard molecular weight markers was sought, to design further mutagenesis experiments to localize TSHR cleavage Site 1. A series of TSHR ectodomain variants, truncated at their C termini at the RK clusters previously considered as potential cleavage sites (shown in FIG. 5) (with 6 histidine C terminal additons) provided ideal molecular weight markers because they, obviously, contain amino acid residues identical to the TSHR A subunit. After engoglycosidase F digestion, immunoblotting established the TSHR A subunit to be clearly smaller than TSHR-309-6H and larger than TSHR-289-6H (see FIG. 5). Therefore, in contrast to previous deductions based on conventional markers, cleavage Site 1 appears to be upstream of TSHR residue 317.

In additon, strong evidenec in favor of Site 1 being upstream of residue 317 was the fact that trypsin clips only a small (1–2 kDa) fragment from the a subunit polypeptide chain that contains the glycan moiety at N302 (see FIG. 2). Thus, even if trypsin is clipping at the most proximal site upstream of the N302 glycan (residues 290–293), spontaneous A subunit cleavage downstream of the N302 glycan is unlikely to be as far as residue 317 (see FIG. 4).

EXAMPLE 3

TSH Receptor Mutations

Mutagenesis In the Vicinity of TSHR Cleavage Sites 1 and 2

All the following mutations (see FIG. 6) were introduced into a TSHR unable to cleave at Site 2 (GQE$_{367-369}$NET) (Kakinuma et al., J. Biol. Chem (in press)) as follows:-(i) For RK$_{312-313}$QQ (previously termed CS3) (Chazebalk, supra), the Mlu I-Eco RV fragment was substituted for the same fragment in TSHR-GQE$_{367-369}$NET; (ii) The "D4" mutation involved the substitution of the D4 segment (amino acid residues 298–308) of the TSHR with the homologous region of the LH/CGR. For this, the Mlu I-Eco RV fragment from TSH-LHR-D4 (13) was used to replace the same fragment in TSHR-GQE$_{367-369}$NET; (iii) The "D5" mutation from TSHR-LHR-D5, involving the substitution of TSHR residues 309–316 with those of the LH/CGR (13) was introduced into TSHR-GQE$_{367-369}$NET by the same approach as for D4; (iv) An RK$_{313-314}$QQ replacement in TSH-LHR-D5-GQE$_{367-369}$NET (iii, above) was generated by PCR using overlapping primers and Pfu DNA polymerase (Stratagene, San Diego, Calif.); (v) Four receptor mutants involved alanine substitutions in the TSHR region between residues 305–316 (AAAA$_{305-308}$, AAAA$_{309-312}$, AAAA$_{310-313}$ and AAAA$_{314-316}$) and, (vi) deletion of amino acid residues 317–366 were also introduced into TSHR-GQE$_{367-369}$NET by PCR using the same approach. The nucleotide sequences of the PCR fragments were confirmed by the dideoxynucleotide termination method (14).

Plasmids were stably transfected with Superfect (Qiagen, Santa Clarita Calif.) into CHO cells cultured as described above. Selection was with 400 μg/ml G418 (GIBCO, Gaithersville Md.). Surviving clones (>100 per 100 mm diameter culture dish) were pooled and propagated for further study.

Estimation of cleavage Site 1 (see above) prompted further mutagenesis in the region between residues 302 and 316. In order to use a "readout" of loss of cleavage by TSH cross-liking to TSHR on the surface of intact cells, all mutations (FIG. 6) were performed on a background of a TSHR unable to cleave at Site 2 (GQE$_{367-369}$NET) (Chazenbalk et al., supra).

Figure 6:
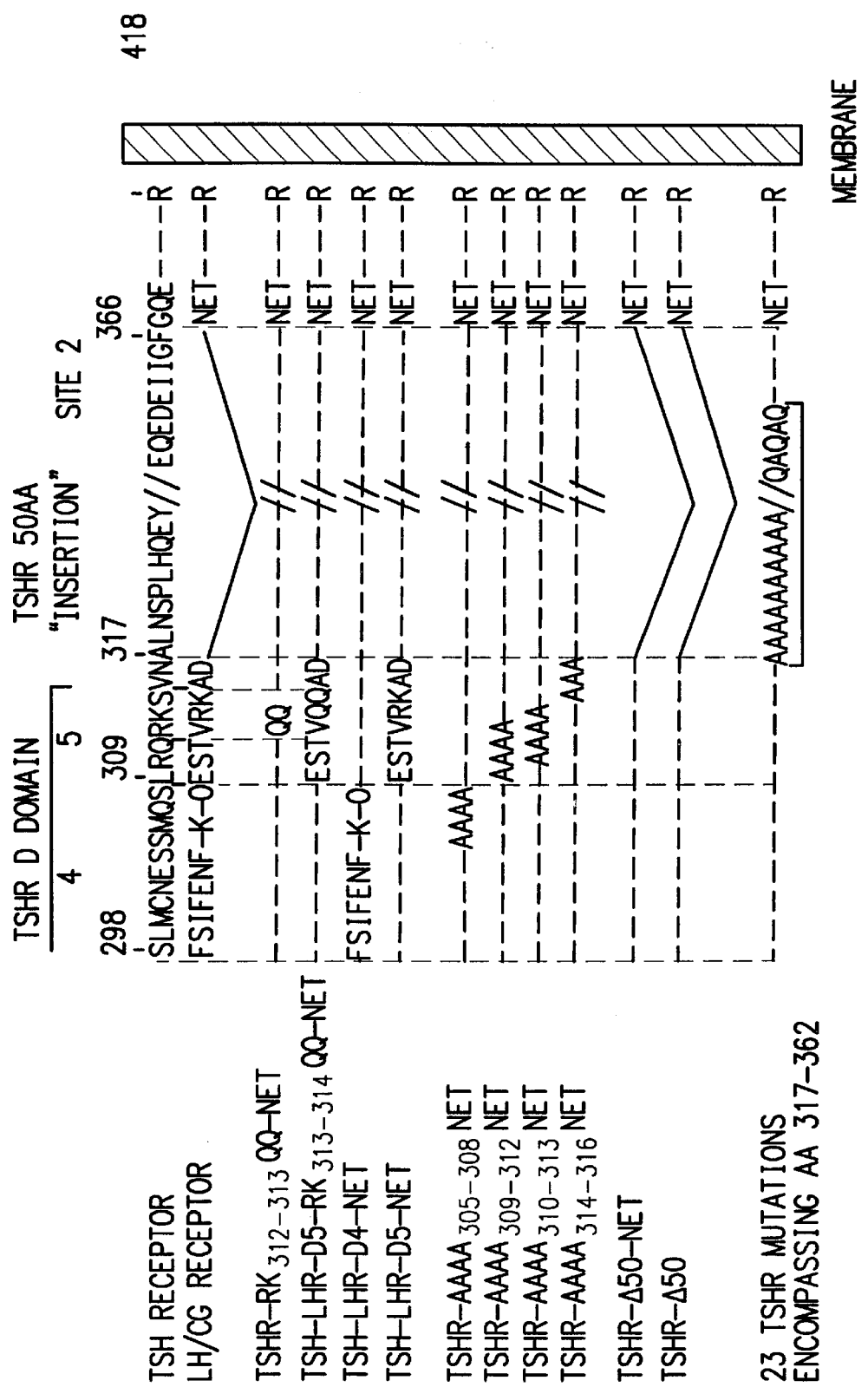
FIG. 6: is a diagrammatic representation showing amino acid substitutions introduced into the vicinity of cleavage Site 1 in the TSHR.
Figure 7:
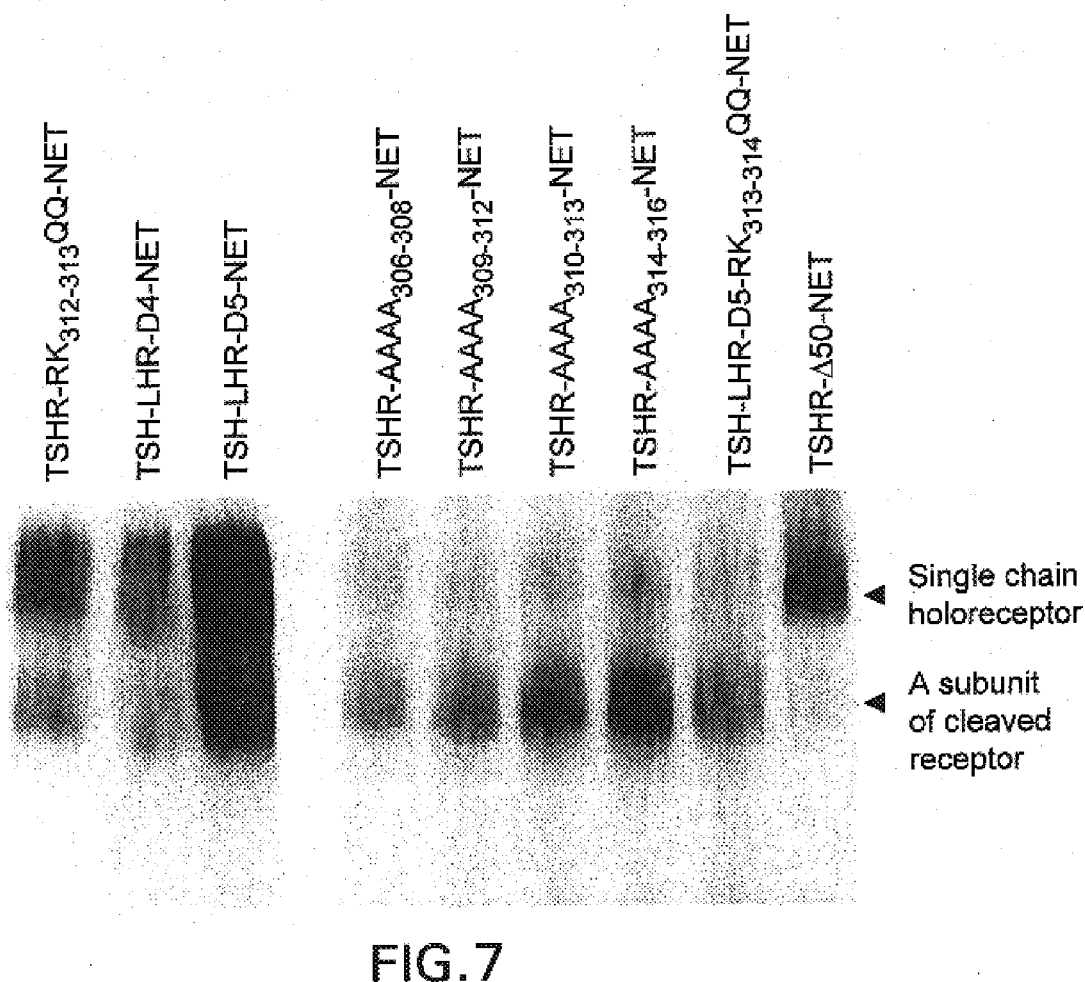
FIG. 7: is a representation of an autoradiograph showing radiolabeled TSH crosslinking to CHO cells stably expressing the receptors described in FIG. 6.

Cleavage into subunits after RK$_{312-313}$QQ substitutions in the wild-type TSHR had been previously reported. Combination of these mutations with GQE$_{367-369}$NET (TSHR-RK$_{312-313}$QQ-NET) did not abolish cleavage at Site 1. Thus, both single chain and two-subunit forms of the TSHR were detected by $^{125}$I-TSH crosslinking (FIG. 7). The region between residues 298 and 316 was then targeted using receptors TSH-LHR-D4-NET and TSH-LHR-D5-NET that involve replacement of every amino acid, except two (S305 and Q307), with the homologous residues of the non-cleaving LH/CGR (FIG. 6). Cleavage at Site 1 was unaltered (FIG. 7). Beacuse of the presence of an RK motif in the LH/CGR in TSH-LHR-D5-NET, we replaced these residues (TSH-LHR-D5-RK$_{313,314}$QQ-NET), again without affecting cleavage at Site 1. For "insurance" we replaced with A all TSHR residues between 305 and 316, including the two residues not previously altered (S305 and Q307). None of the mutations prevented TSHR cleavage at Site 1.

Finally, having mutated every single TSHR residue between 298 and 362, we hypothesized that cleavage at Site 1 did not involve amino acid specificity at the site itself, but involved a distal region or mechanism. One potential region was the 50 amino acid segment unique to the TSHR (residues 317–366). Support for this concept was our previous abrogation of Site 1 cleavage by replacing, on a $GQE_{367-369}NET$ background, the entire TSHR D domain (residues 261–362) (Nagayama et al., Proc. Natl. Acad. Sci. USA 88:902–905 (1991)) with the corresponding region of the LH/CGR. The LH/CGR D domain lacks most of the 50 amino acid TSHR "insertion". Previous evidence against a role for the 50 amino acid insertion in TSHR cleavage was that deletion of this entire segment did not abrogate cleavage into two subunits. However, this deletion had been performed in the wild-type TSHR prior to our discovery of two cleavage sites. Therefore, in the present study, we deleted residues 317–366 in a receptor unable to cleave at Site 2 (TSHR-D50-NET). Cleavage at Site 1 was largely abolished (FIG. 7).

EXAMPLE 4

Immunoprecipitation of Precursor-Labeled TSHR

TSHR-10,000 cells near confluence in 60 mm diameter culture dishes were rinsed with phosphate-buffered saline (PBS) and pre-incubated (0.5 h, twice) in DME-H21 methionine- and cysteine-free medium containing 5% heat-inactivated FCS. The cells were then pulsed (1 h at 37° C.) in 2 ml fresh medium supplemented with 0.2 mCi/ml of $^{35}$S-methionine/cysteine (>1000 Ci/mmole, DuPont NEN, Wilmington Del.). After aspiration of the medium and rinsing the cells once with PBS, chase was performed for 14–16 hours (overnight) in standard, non-selective medium with 10% FCS. Cells were treated for the indicated times at 37° C. with 100 mg/ml trypsin (Sigma, St. Louis Mo.) in Krebs Ringer Hepes buffer, with or without the additon of trypsin inhibitor (100 mg/ml)(Sigma), exactly as described by Van Sande et al. (Van Sande et al., Mol. & Cellular Endo 119:161–168 (1996)). Cells were washed twice with PBS and scraped into 1 ml ice-cold 20 mM Hepes, pH 7.2, 150 mM NaCl (buffer A) and processed as described previously in detail. Mouse monoclonal antibodies (mAb) A10 and A11, obtained fffom of Dr. Banga's laboratory, Kings College, London, U.K.), were used at a final dilution of 1:1000. Samples were resuspended in Laemmli sample buffer (Laemmli et al., Nature 227:680–685 (1970)) with 0.7 M β-mercaptoethanol (30 min at 50° C.) and electrophoresed on 10% SDS-polyacrylamide gels (BioRad, Hercules, Calif.). Prestained molecular weight markers (BioRad) were included in parallel lanes. We precalibrated these markers against more accurate unstained markers to obtain the molecular weights indicated in the text. Radiolabeled proteins were visualized by autoradiography on Biomax MS X-ray film (Eastman Kodak, Rochester, N.Y.)

EXAMPLE 5

Immunoblots of TSHR Proteins

TSHR-10,000 cells in 100 mm diameter dishes were treated for 2 minutes with trypsin in the presence or absence of trypsin inhibitor, as described above. Cells were then scraped and processed as described previously (Chazenbalk et al., Endorinology 138:28938–2899 (1977)). Samples, dissolved in Laemmli buffer with 0.7 M β-mercaptoethanol were electrophoresed on 10% SDS-polyacrylamide gels using prestained molecular weight markers as described above. Proteins were transferred to ProBlot membranes (Applied Biosystems, Foster City, Calif.), which were processed as described previously (Rapoport et al., J. Clin. Endocrinol. Metab. 81:2525–2533 (1996)). Membranes were incubated overnight (4° C.) with mAb A10, A11 or A9 (obtained from Dr. Banga's laboratory)(final dilutions of 1:1000).

EXAMPLE 6

Enzymatic Deglycosylation of TSHR Protein

Where indicated, prior to the additon of Laemmli buffer, the Protein A/IgG/TSHR complex (immunoprecipitations), the 10,000× g crude membrane fractions (immunoblots) or concanavalin A enriched TSHR-261, TSHR-289 and TSHR-309 ectodomain variants (Chazenbalk, et al., J. Biol. Chem 272:18959–18965 (1996)) were treated (10 min, 100° C.) in denaturing buffer containing 0.5% SDS, 1% β-mercaptoethanol, according to the protocol of the manufacturer (N.E. Biolabs Beverly Mass.). N-glycosidase F and endoglycosidase H digestions were as described previously (Chazengbalk, supra). Samples were then subjected to SDS-PAGE, as described above.

TSHR-261-6H, TSHR-289-6H and TSHR-309-6H, shown schematically below, were generated in CHO cells and were partially purified from conditioned medium using concanavalin A. These samples, together with a 100–10,000×g particulate fraction of TSHR-10,000 cells were treated with endoglycosidase F, subjected to SDS-PAGE (10%) under reducing conditions, electroblotted onto membranes and probed with a mouse mAb (A10) to the A subunit (amino acids 22–35).

EXAMPLE 7

Covalent Cross-Linking of Radiolabeled TSH

Confluent 100 mm diameter dishes of TSHR-expressing cells were incubated for 2.5 h at 37 C. with ~5 $\mu$Ci $^{125}$I-TSH followed by crosslinking with disuccinimidyl suberate (DDS; 1 mM; Sigma) and processing as described previously in detail (Chazenbalk, supra). After the addition of Laemmli buffer containing 0.7 Mβ-mercaptoethanol (30 min at 50° C.), the samples were subjected to 10% SDS-PAGE and autoradiography as described above.

Cross-linked products were subjected to PAGE (1.5%) under reducing conditions followed by autoradiography. Note that the ligand, $^{125}$I-TSH, binds to the uncleaved, single chain TSH holoreceptor or to the ligand-binding A subunit in the cleaved TSHR, indicating the presence of both cleaved and uncleaved TSHR on the cell surface. The mass of the hormone ligand complex includes one subunit of the ligand, which itself contains two subunits linked by disulfide bonds. Under reducing conditions, only one ligand subunit (~14 kDa) remains covalently linked to the TSHR.

EXAMPLE 8

TSH Receptor Expression

In order to increase the level of receptor expression, the 5' and 3' untranslated regions of chimeric receptor TSH-LHR-5 were deleted by transposing its Afl II-Spe I fragment (domains D and E)(FIG. 1) with the corresponding fragment in TSHR-5'-3'TR-NEO-ECE (Kakinuma et al., Endocrinology 137:2664–2669 (1996)). Mutations in domain D of chimeric receptor TSH-LHR-5 were generated by PCR using overlapping primers and Pfu DNA polymerase (Stratagene, San Diego, Calif.). The nucleotide sequences of the PCR fragments were confirmed by the dideoxynucleotide termination methods (Sanger et al., Proc. Natl. Acad. Sci. USA 74:5463–5467 (1977)). Plasmids were stably transfected with Lipofection (Gibco-BRL, Gaithersburg, Md.) into Chinese hamster ovary (CHO) cells cultured in Ham's F-12 medium supplemented with 10% fetal calf serum (FCS) and standard antibiotics. Selection was with 400 μg/ml G418 (GIBCO). Surviving clones (>100 per 100 mm diameter culture dish) were pooled and propagated for further study.

Mutations in domain E of chimeric receptor TSHR-LHR-4, were done using the E1, E2 and E3 mutations (see FIG. 3A) previously constructed in the wild-type TSHR (Nagayama et al., *Endocriology* 131:548–552 (1992)). These mutations were transposed into the cDNA for TSH-LHR-4 (Eco RV-Xba I fragment). Subsequent finer mutations in the E domain of TSH-LHR-4 were made by PCR using overlapping primers, with replacement of the Afl II-Spe I fragment. The nucleotide sequences of all PCR products were confirmed and stably-transfected CHO cell lines were generated as described for the domain D mutations.

EXAMPLE 9

Covalent Cross-linking of Radiolabeled TSH

Highly purified bovine TSH (5 μg, 30 U/mg protein) was radiolabeled with $^{125}$I to a specific activity of ~80 μCi/μg protein using the Bolton-Hunter reagent (4400 Ci/mmol; Dupont-NEN) according to the protocol of the manufacturer. confluent 100 mm diameter dishes of TSHR-expressing cells were incubated for 2 h at 37 C. with 5 μCi $^{125}$I-TSH in 5 ml modified Hank's buffer (without NaCl), supplemented with 280 mM sucrose and 0.25% BSA (binding buffer). Unbound $^{125}$I-TSH was removed by rinsing the cells three times with ice-cold binding buffer. Disuccinimidly suberate (DDS) 1 mM; (Sigma) in 10 mM Na phosphate buffer, pH 7.4, containing the protease inhibitors phenylmethylsulfonyl fluoride (PMSF) (100 μg/ml), leupeptin (1 g/ml) aprotinin (1 μg/ml), and pepstatin A (2 μg/ml) (all front Sigma, St. Louis, Mo.) was then added for 20 min at room temperature. The cross-linking reaction was terminated by the addition of 20 mM ammonium acetate (final concentration).

After cross-linking, the cells were rinsed twice with PBS and scraped into 10 mM Tris, pH 7.5, containing the same protease inhibitors. Cells were homogenized using a Polytron homogenizer and centrifuged for 5 min at 4° C. (500× g). The supernatant was centrifuged (15 min, 10,00×g, 4° C.) and the pellet was resuspended in 50 μl 10 mM Tris, pH 7.5. After the addition of Laemmli buffer containing 0.7 M β-mercaptoethanol (30 min at 42° C.), the samples were subjected to 7.5% or 10% SDS-PAGE and autoradiography using Kodak XAR-5 X-ray film (Eastman Kodak, Rochester, N.Y.).

Figure 8:
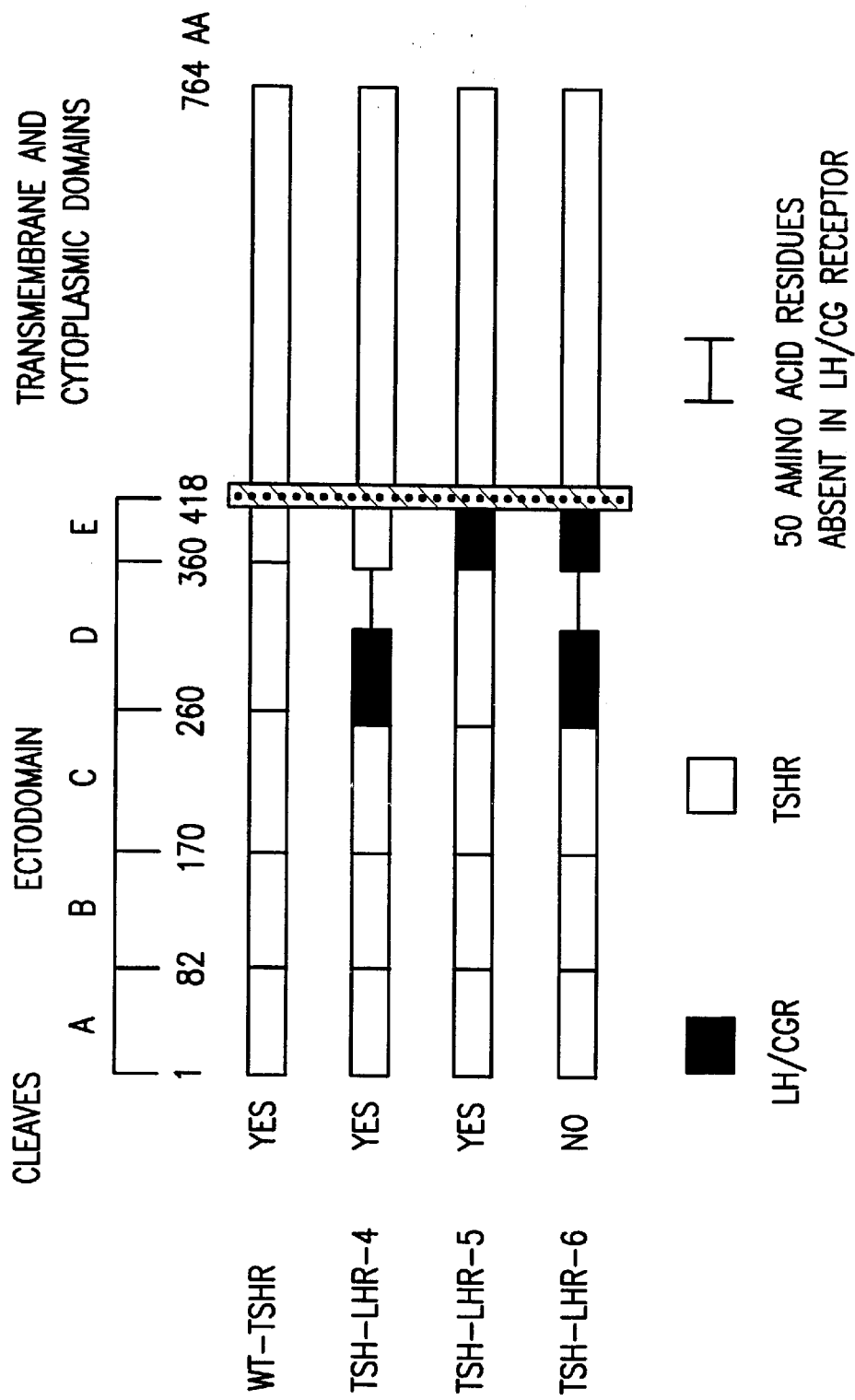
FIG. 8: is a diagramatic representation showing the ectodomain of the TSHR is shown divided into 5 arbitrary domains (A through E) that were used in creating chimeric TSH-LH/CG receptor molecules (19). Three chimeric receptors that are relevant to the present study are indicated. Note that amino acid receptors 317–366 are not present in the LH/CG receptor. Therefore, when domain D of the TSHR is replaced with the corresponding segment of the LH/CG receptor, residues 317–360 are missing.

The basis for the present study was our previous observation that cleavage into A and B subunits did not occur in a chimeric receptor (TSH-LHR-6)(FIG. 8) in which the carboxyl terminal portion of the TSHR ectodomain (amino acid residues 261–418; arbitrary domains "D and E") was replaced with the corresponding region of the LH/CG receptor (Nagayama, et al, Proc. Natl. Acad. Sci. USA 88:902–905 (1991); Russo supra). On the other hand, cleavage still occurred when either domain D or domain E (residues 261–360 and 363–418; chimeric receptors TSH-LHR-4 and TSH-LHR-5, respectively) were substituted on an individual basis. These data, together with other information (Chazenbalk, supra), suggested that cleavage sites 1 and 2 were in TSHR domains D and E, respectively.

Because elimination by mutagenesis of only one cleavage site would not be sufficient to abrogate receptor cleavage, we mutated regions in the vicinity of putative site 1 on a background of TSH-LHR-5. Conversely, regions in the vicinity of putative site 2 were mutagenized on a background of TSH-LHR-4. By this means, it was possible to determine the structural significance of each mutation on receptor cleavage into subunits, as determined by $^{125}$I-TSH crosslinking to monolayers of intact, stably-transferred cells. TSHR residues were replaced with the homologous residues of the non-cleaving LH/CG receptor. Residues common to both receptors were unaltered. In the case of a 50 amino acid region that is unique to the TSHR and lacking in the LH/CG receptor (Nagayama, Biochem. Piophys. Res. Comm. 165:1184–1190 (1989)) (FIG. 6), alanine residues were introduced in most instances. It is noteworthy that this 50 amino acid segment (estimated to be between residues 317–366) is very hydrophilic and can be deleted from the wild-type TSHR without loss of ligand binding and function (Wadsworth et al., Science 249:1423–1425 (1990)) and without preventing cleavage into A and B subunits (Russo, supra).

Figure 9B:
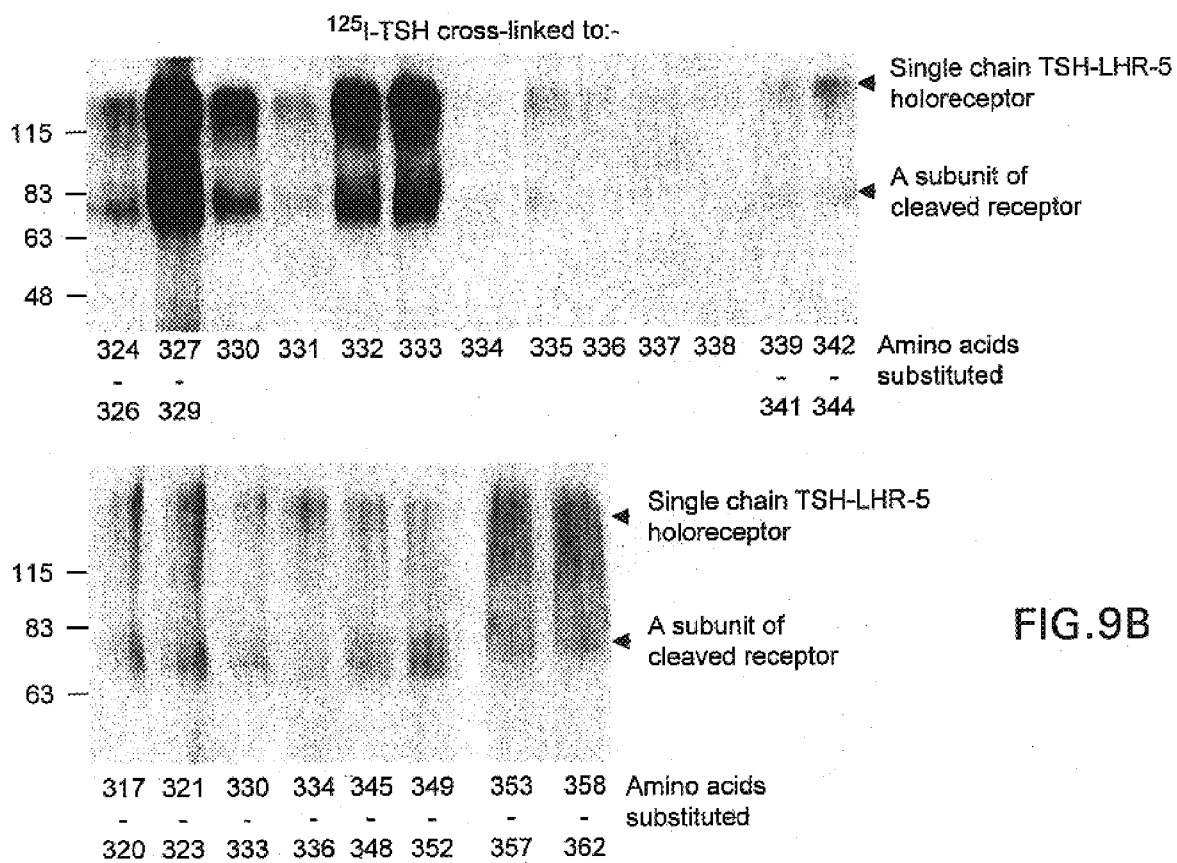
FIG. 9: Panel A: is a diagrammatic representation showing amino acid substitutions introduced in the region of putative cleavage site 1 in the TSHR. Mutations were made in the D domain of chimeric receptor TSH-LHR-5 (FIG. 8). The dashed line for the LH/CG receptor indicates that this region is unique to the TSHR and is absent in the LH/CG receptor.

The deglycosylated TSHR A subunit is ~35 kDa in size (18,25), which would place cleavage site 1 at approximately amino acid residue 335 (numbering includes a 21 residue signal peptide). Residue 330–338 were targeted for alanine scanning mutagenesis (FIG. 9A). None of these individual substitutions prevented cleavance of chimeric receptor TSH-LHR-5, as determined by release of the TSH-linked A subunit on disulfide bond reduction (FIG. 9B). Note that, consistent with previous TSH cross-linking studies to intact cells only a portion of the TSHR on the cell surface cleave into two subunits, with TSH also binding to single polypeptide chain TSHR. Because of the possibility that a single amino acid residue may be insufficient to disrupt a cleavage site, we next performed multiple substitutions over a wider area between residues 324 and 352, also without abolishing cleavage. Finally, we mutagenized TSH-LHR-5 was mutagenetized even further afield (residues 317–323), well upstream of the calculated cleavage site and up to the carboxy-terminus of the domain (residues 353–362), also without effect (FIG. 9B).

Cross-linked products were subjected to PAGE (7.5%) under reducing conditions followed by autoradiography. Note that the ligand, $^{125}$I-TSH, binds to the uncleaved TSH holoreceptor or the ligand-binding A subunit in the cleaved TSHR, indicating the presence of both cleaved and uncleaved TSHR on the cell surface. The mass of the hormone ligand complex includes one subunit of the ligand, which itself contains two subunits linked by disulfide bonds. Under reducing conditions, only one ligand subunit (~14 kDa) remains covalently linked to the TSHR.

Mutagenesis of TSH-LHR-4 (FIG. 10A) identified residues 367–375 (E1 subdomain) as being related to TSHR subunit formation (FIG. 10B). Subdivision of the E1 region into two segments next identified residues 367–371 (E1a segment) to be associated with ectodomain cleavage. The subsequent substitution of individual alanines at residues 376, 368, 369 and 371 (residue 370 being conserved) did not prevented cleavage, suggesting that multiple amino acids contributed to this event. Therefore, to refine further the cleavage-related residues, two overlapping mutants with the E1a segment, E1a1(GQE$_{367-369}$NET) and E1a2 (ELK$_{369-371}$T-Y)(FIG. 3A) were engineered. Abrogation of cleavage in the former identified residues 367–369 to be involved in cleavage at putatibe site 2 (FIG. 10B).

In order to exclude the possibility of only a single cleavage site, the E1a1 mutation (GQE$_{367-369}$NET), known to prevent cleavage of TSH-LHR-4 was introduced, into the wild-type TSHR. Thus, if this segment was the sole site related to TSHR cleavage, its introduction into the wild-type TSHR should prevent cleavage. Conversely, if cleavage still occurred in the wild-type TSHR harboring the GQE$_{367-369}$NET mutation, there must be two cleavage sites in the TSHR ectodomain. Cross-linking of $^{125}$I-TSH to this new construct clearly indicated cleavage (FIG. 11), providing the existence of cleavage site 1.

Remarkably, the mutation (GQE$_{367-369}$NET) that abrogates cleavage at site 2 introduces a consensus sequence for an N-Linked glycosylation site (N-X-S/T). A carbohydrate side-chain in this vicinity could, therefore, prevent ectodomain cleavage, for example by steric hindrance of a cleavage enzyme. As mentioned above, the mutagenesis strategy used to investigate cleavage site 2 in the TSHR involved substitution into the TSHR of the corresponding segments of the non-cleaving LH/CG receptor. The GQE$_{367-369}$NET substitution in the TSHR transposes NET$_{291-293}$ from the LH/CG receptor; a motif that is glycosylated in the latter receptor (Davis et al., Mol. Endocrinol. 11:550–562). In order to determine the functional significance of the GQE$_{367-369}$NET substitution in TSH-LHR-4, a motif (AAA) that would not be a potential glycosylation site was introduced in this chemeric receptor (FIG. 10A). In contrast to the non-cleaving receptor, TSH-LHR-4-GQE$_{367-369}$AAA did cleave (FIG. 10B).

Attempts to determine directly by immunoblotting or immunoprecipitation whether or not the GQE$_{367-369}$NET substitution in TSH-LHR-4 was caused by the introduction of an N-linked glycan were non-informative. Thus, two antibodies to the B subunit that we obtained did not definitively identify the B subunit because of a weak signal and the presence of many other bands (presumably synthetic or degradation products) in cell homogenates. These observations reinforced the value of $^{125}$I-TSH crosslinking to intact cells which only see mature receptor on the cell surface. We, therefore, introduced additional mutations at the GQE$_{367-369}$ triplet in order to explore further the possibility role of N-linked glycosylation at this site upon substitution with NET. Consistent with this hypothesis, the mutation GQE$_{367-369}$NQE (not an N-linked glycosylation motif) in TSHR-LHR-4, unlike in the wild-type TSHR, did not prevent cleavage (FIGS. 11A and B). Further, a GQE$_{367-369}$NQT substitution (an alternative N-linked glycan motif) largely (FIG. 11A) or completely (FIG. 11B) eliminated receptor cleavage. Partial inhibition of receptor cleavage with the NQT versus the NET mutation may be explained by recent evidence that the middle residue ("X") in the N-X-S/T motif has a major effect on the efficiency of N-linked glycosylation (Shakin-Eshalman et al., J. Biol. Chem 271:6363–6366 (1996)).

The evolutionary divergence of the TSHR into a receptor that cleaves into two subunits is unique and enigmatic. Unlike thrombin (Vu et al., Cell 64:1057–1068 (1991)), TSH does not cleave its receptor; two subunit TSHR are present in transfected cells cultured in the absence of TSH (Russo, supra, Mirashi et al.). TSH binds to both cleaved and uncleaved forms of the TSHR. Moreover, TSH action does not require a cleaved receptor (Chazelbalk, supra; Russo, supra). One possibility is that TSHR receptor cleavage, including the release of a small polypeptide between cleavage sites 1 and 2 may be related to the very common occurrence of disease-causing autoantibodies, a phenomenon rarely, if ever, encountered with other members of the G protein-coupled receptor family.

In summary, data obtained from thirty three new TSHR variants stably expressed in CHO cells show the presence of two cleavage sites in the TSHR and identify three amino acid residues in the TSHR that, when substituted with the homologous residues of the LH/CG receptor, prevent cleavage at the second, downstream cleavage site (site 2), and, reveal that cleavage or non-cleavage at this second site is mudulated by to N-linked glycosylation. To our knowledge, the presence or absence of glycosylation represents a novel mechanism by which two closely-related receptors have envolved into having a difference in subunit structure. Greater understanding of its structural features will also contribute to a better understanding of why the TSHR is a pivotal autoantigen in human autoimmune disease.

What is claimed is:

1. A recombinant nucleic acid sequence identical to SEQ ID NO: 54 with the exception of having;
   A nucleic acid sequence region encoding for amino acids 317 to 366 deleted from said recombinant nucleic acid sequence.

2. A recombinant nucleic acid sequence identical to SEQ ID NO: 54 with the exception of having:
   a nucleic acid sequence region encoding for GQE at position 367 to 369 of amino acid sequence SEQ ID NO: 53 replaced with a nucleic acid sequence region encoding for NET or NQT at the 376 to 369 position instead.

3. A recombinant nucleic acid sequence identical to SEQ ID NO: 54 with the exception of having:
   a nucleic acid sequence region encoding for amino acids 317 to 366 deleted from said recombinant nucleic acid sequence; and
   a nucleic acid sequence region encoding for GQE at position 367 to 369 of amino acid sequence SEQ ID NO: 53 replaced with a nucleic acid sequence region encoding for NET or NQT at the 376 to 369 position instead.

* * * * *

UNITED STATES PATENT AND TRADEMARK OFFICE
CERTIFICATE OF CORRECTION

PATENT NO.         : 6,747,139 B1
APPLICATION NO. : 09/186350
DATED               : June 8, 2004
INVENTOR(S)      : Rapoport et al.

It is certified that error appears in the above-identified patent and that said Letters Patent is hereby corrected as shown below:

Column 1

Line 24; "Basdow's" should read --Basedow's--.
    Line 39; "cause, it" should read --cause. It--.

Column 2

Line 8; "(1992);" should read --(1991)--.
    Line 21; "(Lossfelt" should read --(Loosfelt–.
    Line 51; "prevent" should read --prevented--.
    Line 59; delete the comma between the measured and the.

Column 3

Line 5; delete the word "that".
    Line 32; delete the word "is".
    Line 40; after "for" insert the word --more--.

Column 4

Line 27; "transaction" should read --transduction--.
    Line 31; "adenylated" should read --adenylate--.
    Line 59-60; "recominant" should read --recombinant--.

Column 6

Line 34; "Wester" should read --Western--.

Column 7

Line 9; "receptors" should read --residues--.
    Line: 50; "NOT" should read --NQT--.

UNITED STATES PATENT AND TRADEMARK OFFICE
CERTIFICATE OF CORRECTION

PATENT NO. : 6,747,139 B1
APPLICATION NO. : 09/186350
DATED : June 8, 2004
INVENTOR(S) : Rapoport et al.

It is certified that error appears in the above-identified patent and that said Letters Patent is hereby corrected as shown below:

Column 8

Line 17; "replicable" should read --replicatable-- .
    Line 46; after "embodiment," delete the word "in".
    Line 59; after "purpose" change the "," to a --.--.
    Line 66; "plasmid" should read --plasmids--.

Column 9

Line 8; "steptomyces" should read --streptomyces --.
    Line 25; "recominant" should read --recombinant --.

Column 10

Line 46; replicable" should read --replicatable--.

Column 12

Line 41; "or" should read --of--.

Column 13

Line 25; "depressible" should read --derepressible--.
    Line 56; "SP2/O-AG1-4" should read --SP2/0-AG14--.

Column 14

Line 19; "sequence" should read --sequences--.
    Line 62; "(Benoise" should read --(Benoist--.

Column 15

Line 19; after "of" delete the word "the".
    Line 32; after "can" add the word --either--.

Column 16

Line 30; "*Indroduction*" should read --*Introduction*--.
    Line 66; after "respect" change "the" to read --to--.

UNITED STATES PATENT AND TRADEMARK OFFICE
CERTIFICATE OF CORRECTION

PATENT NO. : 6,747,139 B1
APPLICATION NO. : 09/186350
DATED : June 8, 2004
INVENTOR(S) : Rapoport et al.

It is certified that error appears in the above-identified patent and that said Letters Patent is hereby corrected as shown below:

Column 17

Line 16; after "anti" delete the word "and".
      Line 53; "includes" should read --include--.
      Line 63; "type" should read --tope--.

Column 18

Line 1; "detectalby" should read --detectably--.
      Line 3; "antobody" should read --antibody--.

Column 19

Line 30; "known" should read --know--.

Column 20

Line 67; "starct" should read --starch--.

Column 21

Line 49; "vehicels" should read --vehicles--.

Column 22

Line 8; "disease" should read --diseases--.
      Line 45; "anther" should read --another--.

Column 23

Line 2; "threatnes" should read --threatens--.
      Line 44; "1986" should read --1996--.

Column 24

Line 30; after "subunits" delete the word "of".
      Line 48; "Notes" should read --Note--.
      Line 64; "sbunit" should read --subunit--.

UNITED STATES PATENT AND TRADEMARK OFFICE
CERTIFICATE OF CORRECTION

PATENT NO. : 6,747,139 B1
APPLICATION NO. : 09/186350
DATED : June 8, 2004
INVENTOR(S) : Rapoport et al.

It is certified that error appears in the above-identified patent and that said Letters Patent is hereby corrected as shown below:

Column 25

Line 16; "trypsiniation," should read --trypsinization--. Line 29; "samller" should read --smaller--.
Line 54; "engoglycosidase" should read --endoglycosidase--.
Line 62; "after the word "the" "a" should be --A--.

Column 26

Line 10; "(Chazebalk," should read --(Chazenbalk,--.
Line 41; "cross-liking" should read --cross-linking--.

Column 27

Line 57; "Endorinology" should read --Endocrinology--.
Line 57; "138:28938-2899" should read -- 138:2893-2899--.

Column 28

Line 15; "(Chazengbalk," should read --(Chazenbalk,--.
Line 38; "(1.5%)" should read --(7.5%)--.

Column 29

Line 25; "confluent" should read --Confluent--.
Line 33; "1 g/ml)" should read --(1$\mu$g/ml)--.
Line 34; "front" should read --from--.

Column 30

Line 23; "cleavance" should read --cleavage--.
Line 36; after "the" insert --D--.
Line 55; "prevented" should read --prevent--.
Line 61; "putatibe" should read --putative--.

UNITED STATES PATENT AND TRADEMARK OFFICE
CERTIFICATE OF CORRECTION

PATENT NO. : 6,747,139 B1
APPLICATION NO. : 09/186350
DATED : June 8, 2004
INVENTOR(S) : Rapoport et al.

It is certified that error appears in the above-identified patent and that said Letters Patent is hereby corrected as shown below:

Column 31

Line 4; "providing" should read --proving--.

Column 71, line 62; "376" should read --367--.
Column 72, line 60; "376" should read --367--.

Signed and Sealed this

Fifteenth Day of August, 2006

JON W. DUDAS
*Director of the United States Patent and Trademark Office*